US012613624B2

(12) United States Patent
Brouns et al.

(10) Patent No.: US 12,613,624 B2
(45) Date of Patent: Apr. 28, 2026

(54) PLANNING AND/OR CONTROL SYSTEM FOR A NEUROMODULATION SYSTEM

(71) Applicant: ONWARD MEDICAL N.V., Eindhoven (NL)

(72) Inventors: Robin Brouns, Eindhoven (NL); Jurriaan Bakker, Eindhoven (NL); Miroslav Caban, Renens (CH)

(73) Assignee: Onward Medical N.V., Eindhoven (NL)

( * ) Notice: Subject to any disclaimer, the term of this patent is extended or adjusted under 35 U.S.C. 154(b) by 0 days.

(21) Appl. No.: 16/953,322

(22) Filed: Nov. 19, 2020

(65) Prior Publication Data

US 2021/0146140 A1     May 20, 2021

(30) Foreign Application Priority Data

Nov. 19, 2019   (EP) .................................... 19209911

(51) Int. Cl.
A61N 1/36        (2006.01)
A61N 1/05        (2006.01)
(Continued)

(52) U.S. Cl.
CPC ....... G06F 3/04847 (2013.01); A61N 1/0551 (2013.01); A61N 1/36062 (2017.08);
(Continued)

(58) Field of Classification Search
CPC .............. A61N 1/0551; A61N 1/36062; A61N 1/36128; A61N 1/37247; G06F 3/04847; G06F 3/0482; G16H 20/30; G16H 40/63
See application file for complete search history.

(56) References Cited

U.S. PATENT DOCUMENTS 2,868,343 A     1/1959   Sproul
3,543,761 A     12/1970  Bradley
(Continued)

FOREIGN PATENT DOCUMENTS

AU        2012204526 B2     7/2012
CA          2649663 A1     11/2007
(Continued)

OTHER PUBLICATIONS

Communication Pursuant to Article 94(3) EPC in counterpart European Application No. 19209911.7, dated Mar. 1, 2023, (2 pages).
(Continued)

*Primary Examiner* — Joseph M Dietrich
(74) *Attorney, Agent, or Firm* — Finnegan, Henderson, Farabow, Garrett & Dunner, LLP

(57)            ABSTRACT

A planning and/or control system for providing stimulation is disclosed. The system can include a graphical presentation module configured and arranged for providing graphical information about an electrode array comprising multiple electrodes and/or an implantation side for the electrode array comprising at least one target area, a selection module configured and arranged for determining a stimulation zone and/or a stimulation direction on the electrode array comprising at least one electrode and/or for individually selecting at least one electrode and/or for selecting at least one target area, and a calculation module configured and arranged for determining a contribution of currents provided by electrodes of the stimulation zone and/or stimulation direction on the electrode array and/or the at least one electrode selected and/or to the at least one target area selected.

21 Claims, 7 Drawing Sheets

(51) Int. Cl.

| | |
|---|---|
| *A61N 1/372* | (2006.01) |
| *G06F 3/0482* | (2013.01) |
| *G06F 3/04847* | (2022.01) |
| *G16H 20/30* | (2018.01) |
| *G16H 40/63* | (2018.01) |
| *G06F 3/0488* | (2022.01) |

(52) U.S. Cl.
CPC ..... *A61N 1/36125* (2013.01); *A61N 1/36128* (2013.01); *A61N 1/36185* (2013.01); *A61N 1/36189* (2013.01); *A61N 1/37247* (2013.01); *A61N 1/37282* (2013.01); *G06F 3/0482* (2013.01); *G16H 20/30* (2018.01); *G16H 40/63* (2018.01); *G06F 3/0488* (2013.01)

(56) References Cited

U.S. PATENT DOCUMENTS

| | | | |
|---|---|---|---|
| 3,650,277 A | 3/1972 | Sjostrand et al. |
| 3,653,518 A | 4/1972 | Polen |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,303,904 A | 12/1981 | Chasek |
| 4,340,063 A | 7/1982 | Maurer |
| 4,340,216 A | 7/1982 | Murphy |
| 4,356,902 A | 11/1982 | Murphy |
| 4,379,462 A | 4/1983 | Borkan et al. |
| 4,398,537 A | 8/1983 | Holmbo |
| 4,402,501 A | 9/1983 | Lohman |
| 4,410,175 A | 10/1983 | Shamp |
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss et al. |
| 4,569,352 A | 2/1986 | Petrofsky et al. |
| 4,573,481 A | 3/1986 | Bullara |
| 4,574,789 A | 3/1986 | Forster |
| 4,724,842 A | 2/1988 | Charters |
| 4,742,054 A | 5/1988 | Naftchi |
| 4,784,420 A | 11/1988 | Makino et al. |
| 4,798,982 A | 1/1989 | Voorman |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,018,631 A | 5/1991 | Reimer |
| 5,031,618 A | 7/1991 | Mullett |
| 5,066,272 A | 11/1991 | Eaton et al. |
| 5,081,989 A | 1/1992 | Graupe et al. |
| 5,121,754 A | 6/1992 | Mullett |
| 5,284,151 A | 2/1994 | Onoda |
| 5,337,908 A | 8/1994 | Beck, Jr. |
| 5,344,439 A | 9/1994 | Otten |
| 5,348,544 A | 9/1994 | Sweeney et al. |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,421,783 A | 6/1995 | Kockelman et al. |
| 5,441,465 A | 8/1995 | Hefner et al. |
| 5,443,486 A | 8/1995 | Hrdlicka et al. |
| 5,476,441 A | 12/1995 | Durfee et al. |
| 5,553,270 A | 9/1996 | Rosenbluth |
| 5,562,718 A | 10/1996 | Palermo |
| 5,571,141 A | 11/1996 | McNeil et al. |
| 5,584,818 A | 12/1996 | Morrison |
| 5,601,527 A | 2/1997 | Selkowitz |
| 5,626,540 A | 5/1997 | Hall |
| 5,630,836 A | 5/1997 | Prem et al. |
| 5,643,330 A | 7/1997 | Holsheimer et al. |
| 5,643,332 A | 7/1997 | Stein |

| | | | |
|---|---|---|---|
| 5,667,461 A | 9/1997 | Hall |
| 5,733,322 A | 3/1998 | Starkebaum |
| 5,788,606 A | 8/1998 | Rich |
| 5,814,018 A | 9/1998 | Elson et al. |
| 5,819,962 A | 10/1998 | Okubo et al. |
| 5,876,425 A | 3/1999 | Gord et al. |
| 5,877,183 A | 3/1999 | Cincotta |
| 5,948,004 A | 9/1999 | Weijand et al. |
| 5,958,933 A | 9/1999 | Naftchi |
| 5,983,141 A | 11/1999 | Sluijter et al. |
| 5,984,368 A | 11/1999 | Cain |
| 6,052,624 A * | 4/2000 | Mann ................. A61N 1/37247 607/46 |
| 6,058,331 A | 5/2000 | King |
| 6,066,163 A | 5/2000 | John |
| 6,080,087 A | 6/2000 | Bingham |
| 6,104,957 A | 8/2000 | Alo et al. |
| 6,115,634 A | 9/2000 | Donders et al. |
| 6,122,548 A | 9/2000 | Starkebaum et al. |
| 6,139,475 A | 10/2000 | Bessler et al. |
| 6,168,948 B1 | 1/2001 | Anderson et al. |
| 6,182,843 B1 | 2/2001 | Tax et al. |
| 6,188,927 B1 | 2/2001 | Lu et al. |
| 6,236,892 B1 | 5/2001 | Feler |
| 6,280,640 B1 | 8/2001 | Hurwitz et al. |
| 6,281,207 B1 | 8/2001 | Richter et al. |
| 6,308,103 B1 | 10/2001 | Gielen |
| 6,309,401 B1 | 10/2001 | Redko et al. |
| 6,319,241 B1 | 11/2001 | King et al. |
| D454,139 S | 3/2002 | Feldcamp |
| 6,463,327 B1 | 10/2002 | Lurie et al. |
| 6,464,208 B1 | 10/2002 | Smith |
| 6,470,213 B1 | 10/2002 | Alley |
| 6,490,486 B1 | 12/2002 | Bradley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Diagnault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,901,292 B2 | 5/2005 | Hrdlicka et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,978,181 B1 | 12/2005 | Snell |
| 6,988,006 B2 | 1/2006 | King et al. |
| 6,999,820 B2 | 2/2006 | Jordan |
| 7,010,749 B2 | 3/2006 | Hasha et al. |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,099,718 B1 | 8/2006 | Thacker et al. |
| 7,110,820 B2 | 9/2006 | Tcheng et al. |
| 7,125,388 B1 | 10/2006 | Reinkensmeyer et al. |
| 7,127,287 B2 | 10/2006 | Duncan et al. |
| 7,127,296 B2 | 10/2006 | Bradley |
| 7,127,297 B2 | 10/2006 | Law et al. |
| 7,135,497 B1 | 11/2006 | Zeman et al. |
| 7,146,221 B2 | 12/2006 | Krulevitch et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |

(56)                    References Cited

U.S. PATENT DOCUMENTS

| | | |
|---|---|---|
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,330,762 B2 | 2/2008 | Boveja et al. |
| 7,337,005 B2 | 2/2008 | Kim et al. |
| 7,337,006 B2 | 2/2008 | Kim et al. |
| 7,340,298 B1 | 3/2008 | Barbut |
| 7,377,006 B2 | 5/2008 | Genoa et al. |
| 7,381,192 B2 | 6/2008 | Brodard et al. |
| 7,415,309 B2 | 8/2008 | Mcintyre |
| 7,450,992 B1 | 11/2008 | Cameron |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| D594,024 S | 6/2009 | King |
| D595,308 S | 6/2009 | King |
| 7,544,185 B2 | 6/2009 | Bengtsson |
| 7,565,195 B1 | 7/2009 | Kroll et al. |
| 7,584,000 B2 | 9/2009 | Erikson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | De Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,769,464 B2 | 8/2010 | Gerber et al. |
| 7,780,617 B2 | 8/2010 | Tornatore et al. |
| 7,797,057 B2 | 9/2010 | Harris |
| 7,801,600 B1 | 9/2010 | Carbunaru et al. |
| 7,801,601 B2 | 9/2010 | Maschino et al. |
| 7,813,803 B2 | 10/2010 | Heruth et al. |
| 7,813,809 B2 | 10/2010 | Strother et al. |
| 7,840,270 B2 | 11/2010 | Ignagni et al. |
| 7,856,264 B2 | 12/2010 | Firlik et al. |
| 7,861,872 B2 | 1/2011 | Ng et al. |
| 7,877,146 B2 | 1/2011 | Rezai et al. |
| 7,890,182 B2 | 2/2011 | Parramon et al. |
| D638,439 S | 5/2011 | Cavanaugh et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,063,087 B2 | 11/2011 | Chow et al. |
| 8,100,815 B2 | 1/2012 | Balaker et al. |
| 8,108,051 B2 | 1/2012 | Cross, Jr. et al. |
| 8,108,052 B2 | 1/2012 | Boling |
| D656,153 S | 3/2012 | Imamura et al. |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,224,453 B2 | 7/2012 | de Ridder |
| 8,229,565 B2 | 7/2012 | Kim et al. |
| 8,238,666 B2 | 8/2012 | Besley et al. |
| 8,239,038 B2 | 8/2012 | Wolf, II |
| 8,260,436 B2 | 9/2012 | Gerber et al. |
| 8,265,770 B2 | 9/2012 | Toy et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,332,053 B1 | 12/2012 | Patterson et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,374,696 B2 | 2/2013 | Sanchez et al. |
| D677,674 S | 3/2013 | Rampson et al. |
| 8,407,576 B1 | 3/2013 | Yin et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| D684,991 S | 6/2013 | Wenz et al. |
| D684,996 S | 6/2013 | Wenz et al. |
| 8,463,400 B2 * | 6/2013 | Hegi .................. A61N 1/36071 607/117 |
| D688,259 S | 8/2013 | Pearcy et al. |
| D689,086 S | 9/2013 | Philopoulos |
| 8,543,200 B2 | 9/2013 | Lane et al. |
| D691,154 S | 10/2013 | Talbot et al. |
| D691,172 S | 10/2013 | Wujcik et al. |
| 8,588,884 B2 | 11/2013 | Hegde et al. |
| D694,763 S | 12/2013 | Edwards et al. |
| 8,626,300 B2 | 1/2014 | Demarais et al. |
| 8,630,717 B2 | 1/2014 | Olson et al. |
| 8,700,145 B2 | 4/2014 | Kilgard et al. |
| 8,712,546 B2 | 4/2014 | Kim et al. |
| D705,241 S | 5/2014 | Chen et al. |
| D707,235 S | 6/2014 | Arnold et al. |
| 8,740,825 B2 | 6/2014 | Ehrenreich et al. |
| 8,750,957 B2 | 6/2014 | Tang et al. |
| RE45,030 E | 7/2014 | Stevenson et al. |
| 8,766,928 B2 | 7/2014 | Weeldreyer et al. |
| 8,768,472 B2 | 7/2014 | Fang et al. |
| 8,768,481 B2 | 7/2014 | Lane |
| 8,788,046 B2 | 7/2014 | Bennett et al. |
| 8,805,542 B2 | 8/2014 | Tai et al. |
| 8,836,368 B2 | 9/2014 | Afshar et al. |
| 8,847,548 B2 | 9/2014 | Kesler et al. |
| 8,849,410 B2 | 9/2014 | Walker et al. |
| 8,849,418 B2 | 9/2014 | Daglow |
| 8,897,870 B2 | 11/2014 | De Ridder |
| 8,903,502 B2 | 12/2014 | Perryman et al. |
| D721,722 S | 1/2015 | Lee |
| 8,957,549 B2 | 2/2015 | Kesler et al. |
| D735,231 S | 7/2015 | Omiya |
| 9,072,891 B1 | 7/2015 | Rao |
| 9,079,039 B2 | 7/2015 | Carlson et al. |
| 9,101,769 B2 | 8/2015 | Edgerton et al. |
| D737,840 S | 9/2015 | Omiya |
| 9,192,768 B2 | 11/2015 | Yokoi et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| D750,664 S | 3/2016 | Chen et al. |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| D758,398 S | 6/2016 | Yu et al. |
| 9,358,384 B2 | 6/2016 | Dubuclet |
| D760,753 S | 7/2016 | Cheng et al. |
| D762,234 S | 7/2016 | Li et al. |
| 9,393,409 B2 | 7/2016 | Edgerton et al. |
| D763,273 S | 8/2016 | Hwang et al. |
| 9,409,023 B2 | 8/2016 | Burdick et al. |
| 9,409,030 B2 | 8/2016 | Perryman et al. |

(56) References Cited

U.S. PATENT DOCUMENTS

| | | | |
|---|---|---|---|
| 9,415,218 | B2 | 8/2016 | Edgerton et al. |
| 9,421,365 | B2 | 8/2016 | Sumners et al. |
| D769,302 | S | 10/2016 | Rodriguez |
| D770,468 | S | 11/2016 | Carlson et al. |
| D770,470 | S | 11/2016 | Jin |
| 9,520,887 | B1 | 12/2016 | Zhuang et al. |
| D780,768 | S | 3/2017 | Carlson et al. |
| 9,592,358 | B2 | 3/2017 | Miller et al. |
| 9,592,385 | B2 | 3/2017 | Kaula et al. |
| 9,597,517 | B2 | 3/2017 | Moffitt |
| D783,032 | S | 4/2017 | Cashner et al. |
| 9,610,442 | B2 | 4/2017 | Yoo et al. |
| D788,134 | S | 5/2017 | Wong et al. |
| 9,639,982 | B2 | 5/2017 | Craik et al. |
| 9,656,076 | B2 | 5/2017 | Trier et al. |
| D789,963 | S | 6/2017 | Agashiwala et al. |
| D794,667 | S | 8/2017 | Havaldar et al. |
| 9,717,908 | B2 | 8/2017 | Karunasiri |
| 9,724,513 | B2 | 8/2017 | Lane et al. |
| 9,802,052 | B2 | 10/2017 | Marnfeldt |
| 9,812,875 | B2 | 11/2017 | Nejatali et al. |
| D806,717 | S | 1/2018 | Bae et al. |
| 9,895,545 | B2 | 2/2018 | Rao et al. |
| D816,708 | S | 5/2018 | Riedel et al. |
| D819,681 | S | 6/2018 | Fung et al. |
| 9,993,642 | B2 | 6/2018 | Gerasimenko et al. |
| 10,092,750 | B2 | 10/2018 | Edgerton et al. |
| D834,601 | S | 11/2018 | Felt |
| 10,124,166 | B2 | 11/2018 | Edgerton et al. |
| 10,137,299 | B2 | 11/2018 | Lu et al. |
| D839,278 | S | 1/2019 | Carlson et al. |
| D839,914 | S | 2/2019 | Lee et al. |
| D841,017 | S | 2/2019 | Bathla |
| D843,388 | S | 3/2019 | Protzman et al. |
| 10,406,366 | B2 | 9/2019 | Westlund et al. |
| 10,449,371 | B2 | 10/2019 | Serrano Carmona |
| D874,491 | S | 2/2020 | Kuo et al. |
| D874,507 | S | 2/2020 | Martell et al. |
| D875,108 | S | 2/2020 | Chitalia et al. |
| D875,752 | S | 2/2020 | Nelson et al. |
| D877,753 | S | 3/2020 | Chitalia et al. |
| 10,751,533 | B2 | 8/2020 | Edgerton et al. |
| 10,758,732 | B1 | 9/2020 | Heldman |
| 10,773,074 | B2 | 9/2020 | Liu et al. |
| 10,799,701 | B2 | 10/2020 | Lee |
| 10,806,927 | B2 | 10/2020 | Edgerton et al. |
| 10,806,935 | B2 | 10/2020 | Rao et al. |
| D904,437 | S | 12/2020 | Chitalia et al. |
| D905,701 | S | 12/2020 | Feng et al. |
| 10,881,853 | B2 | 1/2021 | Edgerton et al. |
| 10,898,719 | B2 | 1/2021 | Pivonka et al. |
| D912,074 | S | 3/2021 | Giannino et al. |
| D926,784 | S | 8/2021 | Carlson et al. |
| D928,188 | S | 8/2021 | Giannino et al. |
| 11,097,122 | B2 | 8/2021 | Lu |
| 11,123,312 | B2 | 9/2021 | Lu et al. |
| 11,129,983 | B2 | 9/2021 | Lo et al. |
| D939,549 | S | 12/2021 | Miyai et al. |
| D947,216 | S | 3/2022 | Leininger |
| 11,266,850 | B2 | 3/2022 | Prouza et al. |
| 11,298,533 | B2 | 4/2022 | Edgerton et al. |
| D962,245 | S | 8/2022 | Thompson et al. |
| 11,400,284 | B2 | 8/2022 | Gerasimenko et al. |
| 11,491,336 | B2 | 11/2022 | Scheltienne et al. |
| 11,511,116 | B2 | 11/2022 | Wagner et al. |
| 11,515,733 | B2 | 11/2022 | Babakhani et al. |
| 11,638,820 | B2 | 5/2023 | Edgerton et al. |
| 11,684,774 | B2 | 6/2023 | Crosby et al. |
| 11,691,015 | B2 | 7/2023 | Minassian et al. |
| D1,008,290 | S | 12/2023 | Stapfer |
| D1,008,291 | S | 12/2023 | Stapfer |
| D1,010,666 | S | 1/2024 | Cai et al. |
| 11,911,621 | B2 | 2/2024 | Ganty et al. |
| 11,944,814 | B2 | 4/2024 | Lo et al. |
| 11,957,910 | B2 | 4/2024 | Edgerton et al. |
| 11,986,653 | B2 | 5/2024 | Lo et al. |
| 11,992,684 | B2 | 5/2024 | Minassian et al. |
| 12,018,135 | B2 | 6/2024 | Scher et al. |
| 12,023,492 | B2 | 7/2024 | Edgerton et al. |
| 12,076,301 | B2 | 9/2024 | Lu et al. |
| D1,044,827 | S | 10/2024 | Tabrizi et al. |
| 12,201,833 | B2 | 1/2025 | Edgerton et al. |
| 12,214,198 | B2 | 2/2025 | Bennett et al. |
| 12,268,878 | B2 | 4/2025 | Phillips et al. |
| 12,415,079 | B2 | 9/2025 | Scheltienne et al. |
| 2001/0016266 | A1 | 8/2001 | Okazari et al. |
| 2001/0032992 | A1 | 10/2001 | Wendt |
| 2002/0042814 | A1 | 4/2002 | Fukasawa et al. |
| 2002/0050456 | A1 | 5/2002 | Sheppard, Jr. et al. |
| 2002/0052539 | A1 | 5/2002 | Haller et al. |
| 2002/0055779 | A1 | 5/2002 | Andrews |
| 2002/0083240 | A1 | 6/2002 | Hoese et al. |
| 2002/0111661 | A1 | 8/2002 | Cross et al. |
| 2002/0115945 | A1 | 8/2002 | Herman et al. |
| 2002/0123672 | A1 | 9/2002 | Christophersom et al. |
| 2002/0138512 | A1 | 9/2002 | Buresh et al. |
| 2002/0173505 | A1 | 11/2002 | Skogvall |
| 2002/0175931 | A1 | 11/2002 | Holtz et al. |
| 2002/0187260 | A1 | 12/2002 | Sheppard, Jr. et al. |
| 2002/0188332 | A1 | 12/2002 | Lurie et al. |
| 2002/0193843 | A1 | 12/2002 | Hill et al. |
| 2003/0032992 | A1 | 2/2003 | Thacker et al. |
| 2003/0078633 | A1 | 4/2003 | Firlik et al. |
| 2003/0093021 | A1 | 5/2003 | Goffer |
| 2003/0093131 | A1 | 5/2003 | Loeb et al. |
| 2003/0097166 | A1 | 5/2003 | Krulevitch et al. |
| 2003/0100933 | A1 | 5/2003 | Ayal et al. |
| 2003/0113725 | A1 | 6/2003 | Small et al. |
| 2003/0114894 | A1 | 6/2003 | Dar et al. |
| 2003/0114899 | A1 | 6/2003 | Woods et al. |
| 2003/0135253 | A1 | 7/2003 | Kokones et al. |
| 2003/0139422 | A1 | 7/2003 | Teng |
| 2003/0145759 | A1 | 8/2003 | Rodnunsky |
| 2003/0158583 | A1 | 8/2003 | Burnett et al. |
| 2003/0199116 | A1 | 10/2003 | Tai et al. |
| 2003/0200323 | A1 | 10/2003 | Dold et al. |
| 2003/0208248 | A1 | 11/2003 | Carter et al. |
| 2003/0220679 | A1 | 11/2003 | Han |
| 2003/0233137 | A1 | 12/2003 | Paul, Jr. |
| 2004/0039425 | A1 | 2/2004 | Greenwood-Van Meerveld |
| 2004/0044380 | A1 | 3/2004 | Bruninga et al. |
| 2004/0082979 | A1 | 4/2004 | Tong et al. |
| 2004/0087286 | A1 | 5/2004 | Inoue et al. |
| 2004/0088015 | A1 | 5/2004 | Casavant et al. |
| 2004/0111118 | A1 | 6/2004 | Hill et al. |
| 2004/0111126 | A1 | 6/2004 | Tanagho et al. |
| 2004/0121528 | A1 | 6/2004 | Krulevitch et al. |
| 2004/0122483 | A1 | 6/2004 | Nathan et al. |
| 2004/0127954 | A1 | 7/2004 | McDonald, III |
| 2004/0133248 | A1 | 7/2004 | Frei et al. |
| 2004/0138518 | A1 | 7/2004 | Rise et al. |
| 2004/0147975 | A1 | 7/2004 | Popovic et al. |
| 2004/0172027 | A1 | 9/2004 | Speitling et al. |
| 2004/0172097 | A1 | 9/2004 | Brodard et al. |
| 2004/0181263 | A1 | 9/2004 | Balzer et al. |
| 2004/0192082 | A1 | 9/2004 | Wagner et al. |
| 2004/0192834 | A1 | 9/2004 | Nakayoshi et al. |
| 2004/0243204 | A1 | 12/2004 | Maghribi et al. |
| 2004/0267320 | A1 | 12/2004 | Taylor et al. |
| 2005/0004622 | A1 | 1/2005 | Cullen et al. |
| 2005/0043775 | A1 | 2/2005 | John et al. |
| 2005/0061315 | A1 | 3/2005 | Lee et al. |
| 2005/0070982 | A1 | 3/2005 | Heruth et al. |
| 2005/0075662 | A1 | 4/2005 | Pedersen et al. |
| 2005/0075669 | A1 | 4/2005 | King |
| 2005/0075678 | A1 | 4/2005 | Faul |
| 2005/0075693 | A1 | 4/2005 | Toy et al. |
| 2005/0080460 | A1 | 4/2005 | Wang et al. |
| 2005/0090756 | A1 | 4/2005 | Wolf et al. |
| 2005/0101827 | A1 | 5/2005 | Deslisle |
| 2005/0102007 | A1 | 5/2005 | Ayal et al. |
| 2005/0113878 | A1 | 5/2005 | Gerber |
| 2005/0113882 | A1 | 5/2005 | Cameron et al. |
| 2005/0119713 | A1 | 6/2005 | Whitehurst et al. |

(56) References Cited

U.S. PATENT DOCUMENTS

| | | |
|---|---|---|
| 2005/0125045 A1 | 6/2005 | Brighton et al. |
| 2005/0203588 A1 | 9/2005 | King |
| 2005/0205961 A1 | 9/2005 | Doong |
| 2005/0209655 A1 | 9/2005 | Bradley et al. |
| 2005/0231186 A1 | 10/2005 | Saavedra Barrera et al. |
| 2005/0239612 A1 | 10/2005 | Keiser |
| 2005/0246004 A1 | 11/2005 | Cameron et al. |
| 2005/0253273 A1 | 11/2005 | Tai et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0007983 A1 | 1/2006 | Tai et al. |
| 2006/0015153 A1 | 1/2006 | Gliner et al. |
| 2006/0015470 A1 | 1/2006 | Lauer et al. |
| 2006/0016266 A1 | 1/2006 | Weise et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0047325 A1 | 3/2006 | Thimineur et al. |
| 2006/0075339 A1 | 4/2006 | Tomita et al. |
| 2006/0082626 A1 | 4/2006 | Oikawa et al. |
| 2006/0089696 A1 | 4/2006 | Olsen et al. |
| 2006/0095088 A1 | 5/2006 | De Ridder |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189453 A1 | 8/2006 | Leblond |
| 2006/0189839 A1 | 8/2006 | Laniado et al. |
| 2006/0195153 A1 | 8/2006 | DiUbaldi et al. |
| 2006/0239482 A1 | 10/2006 | Hatoum et al. |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0009968 A1 | 1/2007 | Cunningham et al. |
| 2007/0016097 A1 | 1/2007 | Farquhar et al. |
| 2007/0016266 A1 | 1/2007 | Paul, Jr. |
| 2007/0016268 A1 | 1/2007 | Carter et al. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055318 A1 | 3/2007 | Forsberg et al. |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0129769 A1 | 6/2007 | Bourget et al. |
| 2007/0142874 A1 | 6/2007 | John |
| 2007/0142878 A1 | 6/2007 | Krulevitch et al. |
| 2007/0150023 A1 | 6/2007 | Ignagni et al. |
| 2007/0150034 A1 | 6/2007 | Rooney et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0250119 A1 | 10/2007 | Tyler et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0282378 A1 | 12/2007 | Huang et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0092911 A1 | 4/2008 | Schulman et al. |
| 2008/0103579 A1 | 5/2008 | Gerber |
| 2008/0105185 A1 | 5/2008 | Kuhlman |
| 2008/0127031 A1 | 5/2008 | Olsson et al. |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183097 A1 | 7/2008 | Leyde et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0255582 A1 | 10/2008 | Harris |
| 2008/0269854 A1 | 10/2008 | Hegland et al. |
| 2008/0275129 A1 | 11/2008 | Lundstedt et al. |
| 2008/0279896 A1 | 11/2008 | Heinen et al. |
| 2008/0287268 A1 | 11/2008 | Hidler |
| 2008/0294211 A1 | 11/2008 | Moffitt |
| 2008/0294226 A1 | 11/2008 | Moffitt et al. |
| 2008/0318733 A1 | 12/2008 | Osler-Weppenaar |
| 2009/0005844 A1 | 1/2009 | Swoyer et al. |
| 2009/0012436 A1 | 1/2009 | Lanfermann et al. |
| 2009/0024186 A1 | 1/2009 | Brockway |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0227925 A1 | 9/2009 | McBean et al. |
| 2009/0229166 A1 | 9/2009 | Sawrie |
| 2009/0254151 A1 | 10/2009 | Anderson et al. |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2009/0312165 A1 | 12/2009 | Rempe |
| 2010/0004715 A1 | 1/2010 | Fahey |
| 2010/0006737 A1 | 1/2010 | Colombo et al. |
| 2010/0008782 A1 | 1/2010 | Danescu et al. |
| 2010/0010646 A1 | 1/2010 | Drew et al. |
| 2010/0016732 A1 | 1/2010 | Wells et al. |
| 2010/0023069 A1 | 1/2010 | Moffitt et al. |
| 2010/0023070 A1 | 1/2010 | Moffitt et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0048358 A1 | 2/2010 | Tchao et al. |
| 2010/0057177 A1 | 3/2010 | Moffitt et al. |
| 2010/0063568 A1 | 3/2010 | Staunton et al. |

(56) References Cited

U.S. PATENT DOCUMENTS

| | | |
|---|---|---|
| 2010/0070007 A1 | 3/2010 | Parker et al. |
| 2010/0070010 A1 | 3/2010 | Simpson |
| 2010/0087782 A1 | 4/2010 | Ghaffari et al. |
| 2010/0094800 A1 | 4/2010 | Sharp |
| 2010/0114205 A1 | 5/2010 | Donofrio et al. |
| 2010/0114239 A1 | 5/2010 | McDonald, III |
| 2010/0116526 A1 | 5/2010 | Arora et al. |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0137943 A1 | 6/2010 | Zhu |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0179562 A1 | 7/2010 | Linker et al. |
| 2010/0185253 A1 | 7/2010 | Dimarco et al. |
| 2010/0191307 A1 | 7/2010 | Fang et al. |
| 2010/0198298 A1 | 8/2010 | Glulhovsky et al. |
| 2010/0217355 A1 | 8/2010 | Tass et al. |
| 2010/0217418 A1 | 8/2010 | Fontanot |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0279606 A1 | 11/2010 | Hillan et al. |
| 2010/0280570 A1 | 11/2010 | Sturm et al. |
| 2010/0298905 A1 | 11/2010 | Simon |
| 2010/0298910 A1 | 11/2010 | Carbunaru et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0324699 A1 | 12/2010 | Herr et al. |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034912 A1 | 2/2011 | de Graff et al. |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0060461 A1 | 3/2011 | Velliste et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0112611 A1 | 5/2011 | Aghassian |
| 2011/0118815 A1 | 5/2011 | Kuzma et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0201944 A1 | 8/2011 | Higgins et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | Degiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224755 A1 | 9/2011 | Arle et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0230747 A1 | 9/2011 | Rogers et al. |
| 2011/0230808 A1 | 9/2011 | Lisowski |
| 2011/0231326 A1 | 9/2011 | Marino |
| 2011/0237221 A1 | 9/2011 | Prakash et al. |
| 2011/0237921 A1 | 9/2011 | Askin, III et al. |
| 2011/0245734 A1 | 10/2011 | Wagner et al. |
| 2011/0260126 A1 | 10/2011 | Willis |
| 2011/0270360 A1 | 11/2011 | Harris et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011222 A1 | 1/2012 | Yasukawa et al. |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0016453 A1 | 1/2012 | Feler et al. |
| 2012/0018249 A1 | 1/2012 | Mehr |
| 2012/0022371 A1 | 1/2012 | Summerton |
| 2012/0022551 A1 | 1/2012 | Staunton et al. |
| 2012/0029528 A1 | 2/2012 | MacDonald et al. |
| 2012/0035684 A1 | 2/2012 | Thompson et al. |
| 2012/0036552 A1 | 2/2012 | Dare et al. |
| 2012/0041518 A1 | 2/2012 | Kim et al. |
| 2012/0052432 A1 | 3/2012 | Matsuura |
| 2012/0053645 A1 | 3/2012 | Ayanoor-Vitikkate et al. |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0116478 A1 | 5/2012 | Buhlmann et al. |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0143281 A1 | 6/2012 | Birkill et al. |
| 2012/0161531 A1 | 6/2012 | Kim |
| 2012/0161721 A1 | 6/2012 | Neethimanickam |
| 2012/0165899 A1 | 6/2012 | Gliner |
| 2012/0168397 A1 | 7/2012 | Lim et al. |
| 2012/0172222 A1 | 7/2012 | Artigas Puerto |
| 2012/0172246 A1 | 7/2012 | Nguyen et al. |
| 2012/0172510 A1 | 7/2012 | Esseghir et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0203246 A1 | 8/2012 | Staunton et al. |
| 2012/0221073 A1 | 8/2012 | Southwell et al. |
| 2012/0232615 A1 | 9/2012 | Barolat et al. |
| 2012/0252380 A1 | 10/2012 | Kawakita |
| 2012/0252874 A1 | 10/2012 | Feinstein et al. |
| 2012/0259380 A1 | 10/2012 | Pyles |
| 2012/0265269 A1* | 10/2012 | Lui ................... A61N 1/37247 |
| | | 715/764 |
| 2012/0271315 A1 | 10/2012 | Pianca et al. |
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310302 A1 | 12/2012 | Bennett et al. |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0006322 A1 | 1/2013 | Tai |

(56) References Cited

U.S. PATENT DOCUMENTS

| 2013/0006793 A1 | 1/2013 | O'Sullivan et al. |
| 2013/0012853 A1 | 1/2013 | Brown |
| 2013/0013041 A1 | 1/2013 | Glukhovsky et al. |
| 2013/0023972 A1 | 1/2013 | Kuzma et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0032508 A1 | 2/2013 | Azuma |
| 2013/0035745 A1 | 2/2013 | Ahmed et al. |
| 2013/0041235 A1 | 2/2013 | Rogers et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0066411 A1 | 3/2013 | Thacker et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116604 A1 | 5/2013 | Morilla et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0150915 A1 | 6/2013 | Kane et al. |
| 2013/0154373 A1 | 6/2013 | Lisuwandi et al. |
| 2013/0158444 A1 | 6/2013 | Herr et al. |
| 2013/0165991 A1 | 6/2013 | Kim et al. |
| 2013/0190143 A1 | 7/2013 | Greenhill et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0226263 A1 | 8/2013 | Kelly et al. |
| 2013/0237948 A1 | 9/2013 | Donders |
| 2013/0245712 A1 | 9/2013 | Simon et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268020 A1 | 10/2013 | Rosenberg et al. |
| 2013/0268021 A1 | 10/2013 | Moffitt |
| 2013/0268041 A1 | 10/2013 | Schulte et al. |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2013/0325081 A1 | 12/2013 | Karst et al. |
| 2013/0325083 A1 | 12/2013 | Bharmi et al. |
| 2013/0345780 A1 | 12/2013 | Tabada et al. |
| 2014/0005753 A1 | 1/2014 | Carbunaru |
| 2014/0031893 A1 | 1/2014 | Walker et al. |
| 2014/0031895 A1 | 1/2014 | Rahimi et al. |
| 2014/0046407 A1 | 2/2014 | Ben-Ezra et al. |
| 2014/0053401 A1 | 2/2014 | Kuzma et al. |
| 2014/0058292 A1 | 2/2014 | Alford et al. |
| 2014/0058490 A1 | 2/2014 | DiMarco |
| 2014/0059499 A1 | 2/2014 | Kim et al. |
| 2014/0066950 A1 | 3/2014 | MacDonald et al. |
| 2014/0067007 A1 | 3/2014 | Drees et al. |
| 2014/0067013 A1 | 3/2014 | Kaula et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0081345 A1 | 3/2014 | Hershey |
| 2014/0087922 A1 | 3/2014 | Bayerlein et al. |
| 2014/0088674 A1 | 3/2014 | Bradley |
| 2014/0100491 A1 | 4/2014 | Hu et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0114385 A1 | 4/2014 | Nijhuis et al. |
| 2014/0124713 A1 | 5/2014 | Majumdar et al. |
| 2014/0142652 A1 | 5/2014 | Francois et al. |
| 2014/0163640 A1 | 6/2014 | Edgerton et al. |
| 2014/0171961 A1 | 6/2014 | Lacey et al. |
| 2014/0172045 A1 | 6/2014 | Yip et al. |
| 2014/0172055 A1 | 6/2014 | Venancio |
| 2014/0180361 A1 | 6/2014 | Burdick et al. |
| 2014/0200387 A1 | 7/2014 | Ahmed |
| 2014/0201905 A1 | 7/2014 | Glukhovsky |
| 2014/0213842 A1 | 7/2014 | Simon et al. |
| 2014/0213844 A1 | 7/2014 | Pilla et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0257016 A1 | 9/2014 | Ahmed |
| 2014/0277271 A1 | 9/2014 | Chan et al. |
| 2014/0296752 A1 | 10/2014 | Edgerton et al. |
| 2014/0303685 A1 | 10/2014 | Rosenberg et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon De Lima et al. |
| 2014/0339909 A1 | 11/2014 | Sugawara |
| 2014/0343623 A1 | 11/2014 | Alves et al. |
| 2014/0344740 A1 | 11/2014 | Kaula et al. |
| 2014/0357936 A1 | 12/2014 | Simon et al. |
| 2014/0359521 A1 | 12/2014 | Lin et al. |
| 2014/0371830 A1 | 12/2014 | Howard et al. |
| 2015/0005167 A1 | 1/2015 | Jung et al. |
| 2015/0005840 A1 | 1/2015 | Pal et al. |
| 2015/0012061 A1 | 1/2015 | Chen |
| 2015/0022143 A1 | 1/2015 | Kim |
| 2015/0032187 A1 | 1/2015 | Ranu et al. |
| 2015/0051674 A1 | 2/2015 | Barner et al. |
| 2015/0057717 A1 | 2/2015 | Wu et al. |
| 2015/0065559 A1 | 3/2015 | Feinstein et al. |
| 2015/0066111 A1 | 3/2015 | Blum et al. |
| 2015/0074997 A1 | 3/2015 | Kuzma et al. |
| 2015/0088212 A1 | 3/2015 | De Ridder |
| 2015/0094734 A1 | 4/2015 | Staunton et al. |
| 2015/0094791 A1 | 4/2015 | Edgell et al. |
| 2015/0120634 A1 | 4/2015 | Tateno |
| 2015/0126120 A1 | 5/2015 | Chen |
| 2015/0148878 A1 | 5/2015 | Yoo et al. |
| 2015/0151114 A1 | 6/2015 | Black et al. |
| 2015/0151126 A1 | 6/2015 | Kishawi et al. |
| 2015/0165226 A1 | 6/2015 | Simon et al. |
| 2015/0174411 A1 | 6/2015 | Ranu |
| 2015/0182784 A1 | 7/2015 | Barriskill et al. |
| 2015/0188592 A1 | 7/2015 | Solondz |
| 2015/0190200 A1 | 7/2015 | Courtine et al. |
| 2015/0190634 A1 | 7/2015 | Rezai et al. |
| 2015/0196231 A1 | 7/2015 | Ziaie et al. |
| 2015/0196241 A1 | 7/2015 | Yekutieli |
| 2015/0200561 A1 | 7/2015 | Lee et al. |
| 2015/0217120 A1 | 8/2015 | Nandra et al. |
| 2015/0224326 A1 | 8/2015 | Toth et al. |
| 2015/0231326 A1 | 8/2015 | Milner et al. |
| 2015/0231396 A1 | 8/2015 | Burdick et al. |
| 2015/0246216 A1 | 9/2015 | Barker |
| 2015/0265830 A1 | 9/2015 | Simon et al. |
| 2015/0268845 A1 | 9/2015 | Endo |
| 2015/0320632 A1 | 11/2015 | Vallery et al. |
| 2015/0328462 A1 | 11/2015 | Griffith |
| 2015/0343199 A1 | 12/2015 | Wechter et al. |
| 2015/0343205 A1 | 12/2015 | Howard et al. |
| 2016/0001096 A1 | 1/2016 | Mishelevich |
| 2016/0005538 A1 | 1/2016 | Koyanagi et al. |
| 2016/0030737 A1 | 2/2016 | Gerasimenko et al. |

(56) References Cited

U.S. PATENT DOCUMENTS

| | | |
|---|---|---|
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0067477 A1 | 3/2016 | Dubuclet |
| 2016/0074663 A1 | 3/2016 | De Ridder |
| 2016/0082261 A1 | 3/2016 | Moffitt et al. |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0136477 A1 | 5/2016 | Bucher et al. |
| 2016/0143588 A1 | 5/2016 | Hoitink et al. |
| 2016/0144167 A1 | 5/2016 | Bakker et al. |
| 2016/0144184 A1 | 5/2016 | Marnfeldt |
| 2016/0157389 A1 | 6/2016 | Hwang |
| 2016/0166828 A1 | 6/2016 | Yu |
| 2016/0175586 A1 | 6/2016 | Edgerton et al. |
| 2016/0197488 A1 | 7/2016 | Hada et al. |
| 2016/0213918 A1 | 7/2016 | Howard et al. |
| 2016/0220813 A1 | 8/2016 | Edgerton et al. |
| 2016/0228706 A1 | 8/2016 | Hershey et al. |
| 2016/0235977 A1 | 8/2016 | Lu et al. |
| 2016/0250461 A1 | 9/2016 | Dubuclet |
| 2016/0263376 A1 | 9/2016 | Yoo et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0291848 A1 | 10/2016 | Hall et al. |
| 2016/0310739 A1 | 10/2016 | Burdick et al. |
| 2016/0339239 A1 | 11/2016 | Yoo et al. |
| 2016/0367827 A1 | 12/2016 | Tahmasian |
| 2017/0007320 A1 | 1/2017 | Levin et al. |
| 2017/0007831 A1 | 1/2017 | Edgerton et al. |
| 2017/0014620 A9 | 1/2017 | Staunton et al. |
| 2017/0014622 A1 | 1/2017 | Bozung et al. |
| 2017/0065814 A1 | 3/2017 | Howard et al. |
| 2017/0079598 A1 | 3/2017 | Stolen et al. |
| 2017/0098951 A1 | 4/2017 | Olgun et al. |
| 2017/0098962 A1 | 4/2017 | Desrosiers |
| 2017/0118722 A1 | 4/2017 | Hong et al. |
| 2017/0128729 A1 | 5/2017 | Netoff et al. |
| 2017/0156662 A1 | 6/2017 | Goodall et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0189686 A1 | 7/2017 | Steinke et al. |
| 2017/0239486 A1 | 8/2017 | Suryavanshi |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0291023 A1 | 10/2017 | Kuzma et al. |
| 2017/0296837 A1 | 10/2017 | Jin |
| 2017/0338570 A1 | 11/2017 | Myers |
| 2017/0348523 A1 | 12/2017 | Rubehn et al. |
| 2017/0348532 A1 | 12/2017 | Moffitt et al. |
| 2017/0354819 A1 | 12/2017 | Bloch et al. |
| 2017/0361093 A1 | 12/2017 | Yoo et al. |
| 2017/0361115 A1 | 12/2017 | Aghassian et al. |
| 2018/0008826 A1 | 1/2018 | Dimarco |
| 2018/0028812 A1 | 2/2018 | Vallejo et al. |
| 2018/0056078 A1* | 3/2018 | Kashyap ............ A61N 1/36071 |
| 2018/0083473 A1 | 3/2018 | Menegoli et al. |
| 2018/0085582 A1 | 3/2018 | Calle et al. |
| 2018/0085583 A1 | 3/2018 | Zhang et al. |
| 2018/0093093 A1* | 4/2018 | Courtine .................. A61B 5/24 |
| 2018/0104479 A1 | 4/2018 | Grill et al. |
| 2018/0110992 A1 | 4/2018 | Parramon et al. |
| 2018/0117334 A1 | 5/2018 | Jung |
| 2018/0125416 A1 | 5/2018 | Schwarz et al. |
| 2018/0125419 A1 | 5/2018 | Yun et al. |
| 2018/0126154 A1 | 5/2018 | Dubuclet |
| 2018/0126155 A1 | 5/2018 | McLaughlin et al. |
| 2018/0133480 A1 | 5/2018 | Annoni et al. |
| 2018/0133481 A1 | 5/2018 | Von Zitzewitz et al. |
| 2018/0153474 A1 | 6/2018 | Aeschlimann et al. |
| 2018/0178008 A1 | 6/2018 | Bouton et al. |
| 2018/0185632 A1 | 7/2018 | Staunton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0214694 A1 | 8/2018 | Parramon |
| 2018/0221620 A1 | 8/2018 | Metzger |
| 2018/0221651 A1 | 8/2018 | Chang et al. |
| 2018/0228421 A1 | 8/2018 | Saab |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0272125 A1 | 9/2018 | Sandhu |
| 2018/0272132 A1 | 9/2018 | Subbaroyan et al. |
| 2018/0280693 A1 | 10/2018 | Edgerton et al. |
| 2018/0280706 A1 | 10/2018 | Maile et al. |
| 2018/0289971 A1 | 10/2018 | Yeh et al. |
| 2018/0294547 A1 | 10/2018 | Park et al. |
| 2018/0318576 A1 | 11/2018 | Bozung et al. |
| 2018/0326220 A1 | 11/2018 | Kaula et al. |
| 2018/0337547 A1 | 11/2018 | Menegoli et al. |
| 2018/0353755 A1 | 12/2018 | Edgerton et al. |
| 2018/0361146 A1 | 12/2018 | Gerasimenko et al. |
| 2018/0367187 A1 | 12/2018 | McFarthing |
| 2018/0369574 A1 | 12/2018 | Dubuclet et al. |
| 2018/0369575 A1 | 12/2018 | Dubuclet et al. |
| 2018/0369576 A1 | 12/2018 | Dubuclet et al. |
| 2019/0001122 A1 | 1/2019 | Ganty et al. |
| 2019/0001139 A1 | 1/2019 | Mishra et al. |
| 2019/0009094 A1 | 1/2019 | Zhang et al. |
| 2019/0017983 A1 | 1/2019 | Smith |
| 2019/0022371 A1 | 1/2019 | Chang et al. |
| 2019/0027257 A1 | 1/2019 | Ghogawala |
| 2019/0033622 A1 | 1/2019 | Olgun et al. |
| 2019/0160294 A1 | 5/2019 | Peterson et al. |
| 2019/0167980 A1 | 6/2019 | Peterson |
| 2019/0167987 A1 | 6/2019 | Lu et al. |
| 2019/0192852 A1 | 6/2019 | De Ridder |
| 2019/0192864 A1 | 6/2019 | Koop et al. |
| 2019/0240468 A1 | 8/2019 | Yun et al. |
| 2019/0247650 A1 | 8/2019 | Tran |
| 2019/0262609 A1 | 8/2019 | Brill et al. |
| 2019/0269917 A1 | 9/2019 | Courtine et al. |
| 2019/0299006 A1 | 10/2019 | Marnfeldt |
| 2019/0321639 A1 | 10/2019 | Rao et al. |
| 2019/0336760 A1 | 11/2019 | Shah |
| 2019/0344070 A1 | 11/2019 | Molnar et al. |
| 2019/0344075 A1 | 11/2019 | Bloch et al. |
| 2019/0358454 A1 | 11/2019 | Lin et al. |
| 2019/0374776 A1 | 12/2019 | Mishra et al. |
| 2019/0374777 A1 | 12/2019 | Burdick et al. |
| 2019/0381313 A1 | 12/2019 | Lu |
| 2019/0381328 A1 | 12/2019 | Wechter et al. |
| 2019/0381382 A1 | 12/2019 | Wu |
| 2020/0009385 A1 | 1/2020 | Shah |
| 2020/0060602 A1 | 2/2020 | Wagner et al. |
| 2020/0061378 A1 | 2/2020 | Ganguly et al. |
| 2020/0086116 A1 | 3/2020 | Formento et al. |
| 2020/0121544 A1 | 4/2020 | George et al. |
| 2020/0139126 A1 | 5/2020 | Napadow et al. |
| 2020/0144846 A1 | 5/2020 | Shin |
| 2020/0147382 A1 | 5/2020 | Caban et al. |
| 2020/0155019 A1 | 5/2020 | Esteller et al. |
| 2020/0155865 A1 | 5/2020 | Lu |
| 2020/0228901 A1 | 7/2020 | Baek |
| 2020/0360697 A1 | 11/2020 | Paoles et al. |
| 2020/0398068 A1 | 12/2020 | Agnihotri et al. |
| 2021/0069052 A1 | 3/2021 | Burke |
| 2021/0093865 A1 | 4/2021 | Vallejo et al. |
| 2021/0121692 A1 | 4/2021 | Edgerton et al. |
| 2021/0153942 A1 | 5/2021 | Scheltienne et al. |
| 2021/0154481 A1 | 5/2021 | Scheltienne et al. |
| 2021/0170177 A1 | 6/2021 | Minassian et al. |
| 2021/0170178 A1 | 6/2021 | Wagner et al. |

(56) References Cited

U.S. PATENT DOCUMENTS

| | | |
|---|---|---|
| 2021/0187278 A1 | 6/2021 | Lu |
| 2021/0213292 A1 | 7/2021 | Minassian et al. |
| 2021/0236837 A1 | 8/2021 | Lu |
| 2021/0275810 A1 | 9/2021 | Caban |
| 2021/0290955 A1 | 9/2021 | Brouns et al. |
| 2021/0299441 A1 | 9/2021 | Edgerton et al. |
| 2021/0378991 A1 | 12/2021 | Lu |
| 2021/0402186 A1 | 12/2021 | Edgerton et al. |
| 2022/0016420 A1 | 1/2022 | Lo et al. |
| 2022/0111208 A1 | 4/2022 | Phillips et al. |
| 2022/0125374 A1 | 4/2022 | Courtine et al. |
| 2022/0134108 A1 | 5/2022 | Dinsmoor et al. |
| 2022/0143407 A1 | 5/2022 | Zhuang et al. |
| 2022/0161042 A1 | 5/2022 | Lu et al. |
| 2022/0176130 A1 | 6/2022 | Wu et al. |
| 2022/0184386 A1 | 6/2022 | Courtine et al. |
| 2022/0233848 A1 | 7/2022 | Gad et al. |
| 2022/0313993 A1 | 10/2022 | Gerasimenko et al. |
| 2022/0409899 A1 | 12/2022 | Ganty et al. |
| 2023/0045403 A1 | 2/2023 | Robison et al. |
| 2023/0053053 A1 | 2/2023 | Delattre et al. |
| 2023/0186201 A1 | 6/2023 | Cella et al. |
| 2023/0281527 A1 | 9/2023 | Cella et al. |
| 2024/0001116 A1 | 1/2024 | Edgerton et al. |
| 2024/0050746 A1 | 2/2024 | Angeli et al. |
| 2024/0335666 A1 | 10/2024 | Murphy |
| 2024/0374541 A1 | 11/2024 | Lu et al. |
| 2024/0424291 A1 | 12/2024 | Ganty et al. |
| 2024/0424302 A1 | 12/2024 | Dumeny |
| 2025/0025689 A1 | 1/2025 | Lo et al. |
| 2025/0032799 A1 | 1/2025 | Weijand et al. |

FOREIGN PATENT DOCUMENTS

| | | |
|---|---|---|
| CA | 2856202 A1 | 5/2013 |
| CA | 2864473 A1 | 5/2013 |
| CA | 3034123 A1 | 2/2018 |
| CA | 2823592 A1 | 11/2021 |
| CN | 101227940 A | 7/2008 |
| CN | 101822223 A | 8/2013 |
| CN | 103263727 A | 8/2013 |
| CN | 104307098 A | 1/2015 |
| DE | 3830429 A1 | 3/1990 |
| DE | 2020007015508 U1 | 3/2008 |
| EP | 0034145 A1 | 8/1981 |
| EP | 0236976 A1 | 9/1987 |
| EP | 0630987 A1 | 12/1994 |
| EP | 1127907 A2 | 8/2001 |
| EP | 1303332 A1 | 4/2003 |
| EP | 1575665 A1 | 9/2005 |
| EP | 1675648 A1 | 7/2006 |
| EP | 1680182 A1 | 7/2006 |
| EP | 2130326 A1 | 12/2009 |
| EP | 2141851 A2 | 1/2010 |
| EP | 2160127 A1 | 3/2010 |
| EP | 2178319 A1 | 4/2010 |
| EP | 2192897 A1 | 6/2010 |
| EP | 2226114 A1 | 9/2010 |
| EP | 2243510 A2 | 10/2010 |
| EP | 2258496 A1 | 12/2010 |
| EP | 2361631 A1 | 8/2011 |
| EP | 2368401 A1 | 9/2011 |
| EP | 2387467 A1 | 11/2011 |
| EP | 2396995 A1 | 12/2011 |
| EP | 2397788 A1 | 12/2011 |
| EP | 2445990 A2 | 5/2012 |
| EP | 2471518 A2 | 7/2012 |
| EP | 2475283 A1 | 7/2012 |
| EP | 2486897 A2 | 8/2012 |
| EP | 2626051 A1 | 8/2013 |
| EP | 2628502 A1 | 8/2013 |
| EP | 2661307 A2 | 11/2013 |
| EP | 2665514 A2 | 11/2013 |
| EP | 2688642 A2 | 1/2014 |
| EP | 2810689 A1 | 12/2014 |

| | | |
|---|---|---|
| EP | 2810690 A1 | 12/2014 |
| EP | 2868323 A1 | 5/2015 |
| EP | 2868343 A1 | 5/2015 |
| EP | 2966422 A1 | 1/2016 |
| EP | 2968940 A1 | 1/2016 |
| EP | 3184145 A1 | 6/2017 |
| EP | 3269424 A1 | 1/2018 |
| EP | 3323468 A1 | 5/2018 |
| EP | 3328481 A1 | 6/2018 |
| EP | 3381506 A1 | 10/2018 |
| EP | 3421081 A1 | 1/2019 |
| EP | 3285855 B1 | 6/2019 |
| EP | 3495019 A1 | 6/2019 |
| EP | 3527258 A1 | 8/2019 |
| EP | 3969100 B1 | 7/2023 |
| JP | H0326620 A | 2/1991 |
| JP | 3184145 B2 | 7/2001 |
| JP | 2002517283 A | 6/2002 |
| JP | 2002200178 A | 7/2002 |
| JP | 2004065529 A | 3/2004 |
| JP | 2007526798 A | 9/2007 |
| JP | 2008067917 A | 3/2008 |
| JP | 2008543429 A | 12/2008 |
| JP | 2009512516 A | 3/2009 |
| JP | 2011502586 A | 1/2011 |
| JP | 2011504112 A | 2/2011 |
| JP | 2012515060 A | 7/2012 |
| JP | 2013508119 A | 3/2013 |
| JP | 2014513562 A | 6/2014 |
| JP | 2014514043 A | 6/2014 |
| JP | 6132856 A | 3/2015 |
| JP | 2016506255 A | 3/2016 |
| JP | 6132856 B2 | 5/2017 |
| JP | 2017104685 A | 6/2017 |
| JP | 2017523868 A | 8/2017 |
| JP | 2017525509 A | 9/2017 |
| JP | 2018524113 A | 8/2018 |
| KR | 101573840 B1 | 12/2015 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2193441 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| RU | 2661307 C1 | 7/2018 |
| WO | 8100458 A1 | 2/1981 |
| WO | WO 1994009808 A1 | 5/1994 |
| WO | WO 1997047357 A1 | 12/1997 |
| WO | WO 199908749 A1 | 2/1999 |
| WO | WO 200019912 A1 | 4/2000 |
| WO | 0209808 A1 | 2/2002 |
| WO | WO 2002/009808 A1 | 2/2002 |
| WO | WO 2002034331 A2 | 5/2002 |
| WO | WO 2002092165 A1 | 11/2002 |
| WO | WO 2003005887 A2 | 1/2003 |
| WO | WO 2003026735 A2 | 4/2003 |
| WO | WO 2003092795 A1 | 11/2003 |
| WO | WO 2003094749 A1 | 11/2003 |
| WO | WO 2004087116 A2 | 10/2004 |
| WO | WO 2005002663 A2 | 1/2005 |
| WO | WO 2005051306 A2 | 6/2005 |
| WO | WO 2005065768 A1 | 7/2005 |
| WO | WO 2005087307 A2 | 9/2005 |
| WO | WO 2006026850 A1 | 3/2006 |
| WO | 2006135751 A2 | 12/2006 |
| WO | WO 2006138069 A1 | 12/2006 |
| WO | 2007007057 A1 | 1/2007 |
| WO | WO 2007007058 A1 | 1/2007 |

(56)                References Cited

FOREIGN PATENT DOCUMENTS

| | | |
|---|---|---|
| WO | WO 2007012114 A1 | 2/2007 |
| WO | WO 2007047852 A2 | 4/2007 |
| WO | WO 2007057508 A2 | 5/2007 |
| WO | WO 2007081764 A2 | 7/2007 |
| WO | WO 2007107831 A2 | 9/2007 |
| WO | WO 2008070807 A3 | 6/2008 |
| WO | WO 2008075294 A1 | 6/2008 |
| WO | WO 2008092785 A1 | 8/2008 |
| WO | WO 2008109862 A2 | 9/2008 |
| WO | WO 2008121891 A1 | 10/2008 |
| WO | WO 2009042217 A1 | 4/2009 |
| WO | WO 2009111142 A2 | 9/2009 |
| WO | WO 2010021977 A1 | 2/2010 |
| WO | WO 2010055421 A1 | 5/2010 |
| WO | 2010083308 A1 | 7/2010 |
| WO | WO 2010114998 A1 | 10/2010 |
| WO | WO 2010124128 A1 | 10/2010 |
| WO | WO 2011005607 A1 | 1/2011 |
| WO | WO 2011008459 A2 | 1/2011 |
| WO | WO 2011136875 A1 | 11/2011 |
| WO | WO 2012075195 A1 | 6/2012 |
| WO | WO 2012080964 A1 | 6/2012 |
| WO | WO 2012094346 A2 | 7/2012 |
| WO | WO 2012100260 A2 | 7/2012 |
| WO | WO 2012103519 A2 | 8/2012 |
| WO | WO 2012129574 A2 | 9/2012 |
| WO | 2013049658 A1 | 4/2013 |
| WO | WO 2013069004 A1 | 5/2013 |
| WO | WO 2013071307 A1 | 5/2013 |
| WO | WO 2013071309 A1 | 5/2013 |
| WO | WO 2013117750 A1 | 8/2013 |
| WO | WO 2013152124 A1 | 10/2013 |
| WO | WO 2013179230 A1 | 12/2013 |
| WO | WO 2013188965 A1 | 12/2013 |
| WO | WO 2014005075 A1 | 1/2014 |
| WO | WO 2014031142 A1 | 2/2014 |
| WO | WO 2014089299 A2 | 6/2014 |
| WO | WO 2014144785 A1 | 9/2014 |
| WO | WO 2014149895 A1 | 9/2014 |
| WO | WO 2014205356 A2 | 12/2014 |
| WO | WO2014209877 A1 | 12/2014 |
| WO | WO 2015000800 A1 | 1/2015 |
| WO | WO 2015048563 A2 | 4/2015 |
| WO | WO 2015063127 A1 | 5/2015 |
| WO | WO 2015106286 A1 | 7/2015 |
| WO | WO 2015172894 A1 | 11/2015 |
| WO | WO 2016005367 A1 | 1/2016 |
| WO | WO 2016025913 A1 | 2/2016 |
| WO | WO 2016029159 A2 | 2/2016 |
| WO | WO 2016033369 A1 | 3/2016 |
| WO | WO 2016033372 A1 | 3/2016 |
| WO | WO 2016064761 A1 | 4/2016 |
| WO | WO 2016110804 A1 | 7/2016 |
| WO | WO 2016112398 A1 | 7/2016 |
| WO | WO2016172239 A1 | 10/2016 |
| WO | WO 2017011410 A1 | 1/2017 |
| WO | WO 20170055661 A1 | 1/2017 |
| WO | WO 2017024276 A1 | 2/2017 |
| WO | WO 2017035512 A1 | 3/2017 |
| WO | WO 2017044904 A1 | 3/2017 |
| WO | WO 2017058913 A1 | 4/2017 |
| WO | WO 2017062508 A1 | 4/2017 |
| WO | WO 2017117450 A1 | 7/2017 |
| WO | WO 2017146659 A1 | 8/2017 |
| WO | WO 2017188965 A1 | 11/2017 |
| WO | WO 2018033591 A2 | 2/2018 |
| WO | 2018039458 A1 | 3/2018 |
| WO | WO 2018039296 A2 | 3/2018 |
| WO | 2018063879 A1 | 4/2018 |
| WO | WO 2018093765 A1 | 5/2018 |
| WO | WO 2018106843 A1 | 6/2018 |
| WO | WO 2018148844 A1 | 8/2018 |
| WO | WO 2018160531 A1 | 8/2018 |
| WO | WO 2018217791 A1 | 11/2018 |
| WO | WO 2012050200 A1 | 4/2019 |
| WO | WO 2019211314 A1 | 11/2019 |
| WO | WO 2020028088 A1 | 2/2020 |
| WO | WO 2020041502 A1 | 2/2020 |
| WO | WO 2020041633 A1 | 2/2020 |
| WO | WO 2020416331 A1 | 2/2020 |
| WO | WO 2020236946 A1 | 11/2020 |
| WO | D215131-0001 | 7/2022 |
| WO | 2022221442 A1 | 10/2022 |

OTHER PUBLICATIONS

Abernethy, J. et al., "Competing in the Dark: An Efficient Algorithm for Bandit Linear Optimization", Conference on Learning Theory, (2008), 13 pages.

Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.

Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 22 pages.

Anderson, K., "Targeting Recovery: Priorities of the Spinal Cord-Injured Population," Journal of Neurotrauma, vol. 21, No. 10, (Oct. 2004), 13 pages.

Angeli, C. et al., "Altering spinal cord excitability enables voluntary movements after chronic complete paralysis in humans," Brain, vol. 137, No. 5, May 2014, Available Online Apr. 8, 2014, 16 pages.

Auer, P. et al., "Finite-time Analysis of the Multiarmed Bandit Problem", Machine Learning, vol. 47, No. 2, (2002), pp. 235-256.

Auer, P. "Using Confidence Bounds for Exploitation-Exploration Trade-offs", Journal of Machine Learning Research, vol. 3, (2002), pp. 397-422.

Azimi, J. et al., "Batch Bayesian Optimization via Simulation Matching", In Advances in Neural Information Processing Systems (NIPS), (2010), 9 pages.

Azimi, J. et al., "Hybrid Batch Bayesian Optimization", In Proceedings of the 29th International Conference on Machine Learning, (2012), 12 pages.

Azimi, J. et al., "Batch Active Learning via Coordinated Matching", In Proceedings of the 29th International Conference on Machine Learning, (2012), 8 pages.

Barbeau, H. et al., "Recovery of locomotion after chronic spinalization in the adult cat", Brain Research, vol. 412, No. 1, (May 26, 1987), 12 pages.

Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.

Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.

Brochu, E. et al., "A Tutorial on Bayesian Optimization of Expensive Cost Functions, with Application to Active User Modeling and Hierarchical Reinforcement Learning", In TR-2009-23, UBC, (2009), 49 pages.

Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.

Bubeck, S. et al., "Online Optimization in X-Armed Bandits", Advances in Neural Information Processing Systems (NIPS), (2008), 8 pages.

Bubeck, S. et al., "Pure Exploration in Finitely-Armed and Continuous-Armed Bandits problems" In ALT, (2009), 35 pages.

Burke, R., "Group la Synaptic Input to Fast and Slow Twitch Motor Units of Cat Triceps Surae", The Journal of Physiology, vol. 196, vol. 3, (Jun. 1, 1968), 26 pages.

Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.

(56) References Cited

OTHER PUBLICATIONS

Capogrosso, M. et al., "A Computational Model for Epidural Electrical Stimulation of Spinal Sensorimotor Circuits", Journal of Neuroscience, Dec. 4, 2013, vol. 33, No. 49, pp. 19326-19340.

Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.

Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.

Courtine, G. et al., "Can experiments in nonhuman primates expedite the translation of treatments for spinal cord injury in humans?", Nature Medicine, vol. 13, No. 5, (May 2007), 13 pages.

Courtine, G. et al., "Recovery of supraspinal control of stepping via indirect propriospinal relay connections after spinal cord injury," Nature Medicine, vol. 14, No. 1, (Jan. 6, 2008), 6 pages.

Courtine, G. et al., "Transformation of nonfunctional spinal circuits into functional states after the loss of brain input," Nature Neuroscience, vol. 12, No. 10, Published Online Sep. 20, 2009, (2009), 12 pages.

Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.

Dani, V. et al., "Stochastic Linear Optimization Under Bandit Feedback", In Proceedings of the 21st Annual Conference on Learning Theory (COLT), (2008), 15 pages.

Danner, S. M. et al., "Body Position Influences Which neural structures are recruited by lumbar transcutaneous spinal cord stimulation", PLoS One, vol. 11, No. 1, (2016), 13 pages.

Danner, S. et al., "Human spinal locomotor control is based on flexibly organized burst generators," Brain, vol. 138, No. 3, Available Online Jan. 12, 2015, (Mar. 2015), 12 pages.

Dimitrijevic, M. M. et al., "Evidence for a Spinal Central Pattern Generator in Humans", Annals New York Academy Sciences, vol. 860, (1998), pp. 360-376.

Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.

Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.

Drew, T. et al., "Cortical mechanisms involved in visuomotor coordination during precision walking," Brain Research Reviews, vol. 57, No. 1, Published Online Aug. 22, 2007, (Jan. 2007), 13 pages.

Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.

Edgerton, V. et al., "Robotic Training and Spinal Cord Plasticity," Brain Research Bulletin, vol. 78, No. 1, Published Online Nov. 14, 2008, (Jan. 15, 2009), 19 pages.

Edgerton, V. et al., "Training Locomotor Networks," Brain Research Reviews, vol. 57, Published Online Sep. 16, 2007, (Jan. 2008), 25 pages.

Fleshman, J. et al., "Electronic Architecture of Type-Identified a-Motoneurons in the Cat Spinal Cord," Journal of Neurophysiology, vol. 60, No. 1, (Jul. 1, 1988), 26 pages.

Frey, M. et al., "A Novel Mechatronic Body Weight Support System," IEEE Transactions on Neural Systems and Rehabilitation Engineering, vol. 14, No. 3, (Sep. 18, 2006), 11 pages.

Fuentes, R. et al., "Spinal Cord Stimulation Restores Locomotion in Animal Models of Parkinson's Disease," Science, vol. 323, No. 5921, (Mar. 20, 2009), 14 pages.

Ganley, K. J. et al., "Epidural Spinal Cord Stimulation Improves Locomotor Performance in Low ASIA C, Wheelchair-Dependent, Spinal Cord-Injured Individuals: Insights from Metabolic Response", Top. Spinal Cord Inj. Rehabil., vol. 11, No. 2, (2005), pp. 60-63.

Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.

Gerasimenko, Yu. P. et al., "Noninvasive Reactivation of Motor Descending Control after Paralysis", Journal of Neurotrauma, vol. 32, (2015), 13 pages.

Gilja, V. et al., "A high-performance neural prosthesis enabled by control algorithm design," Nature Neuroscience, vol. 15, No. 12, Published Online Nov. 18, 2012, (Dec. 2012), 56 pages.

Gittins, J. C., "Bandit Processes and Dynamic Allocation Indices", Journal of the Royal Statistical Society B, vol. 41, No. 2, (1979), pp. 148-177.

Guyatt, G. H. et al., "The 6-minute walk: a new measure of exercise capacity in patients with chronic heart failure," Canadian Medical Association Journal, vol. 132, No. 8, (Apr. 15, 1985), 5 pages.

Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.

Harkema, S. et al., "Effect of Epidural stimulation of the lumbosacral spinal cord on voluntary movement, standing, and assisted stepping after motor complete paraplegia: a case study," Lancet, vol. 377, No. 9781, (Jun. 4, 2011) Available Online May 19, 2011, 17 pages.

Harkema, S. et al., "Human Lumbosacral Spinal Cord Interprets Loading During Stepping," Journal of Neurophysiology, vol. 77, No. 2, (Feb. 1, 1997), 15 pages.

Harrison, P. et al., "Individual Excitatory Post-Synaptic Potentials Due to Muscle Spindle Ia Afferents in Cat Triceps Surae Motoneurones," The Journal of Physiology, vol. 312, No. 1, (Mar. 1981), pp. 455-470.

Hashtrudi-Zaad, K. et al., "On the Use of Local Force Feedback for Transparent Teleoperation," Proceedings of the 1999 IEEE International Conference on Robotics and Automation, (May 10, 1999), 7 pages.

Herman, R. et al., "Spinal cord stimulation facilitates functional walking in a chronic, incomplete spinal cord injured," Spinal Cord, vol. 40, No. 2, (2002), 4 pages.

Hennig, P. et al., "Entropy search for information-efficient global optimization" Journal of Machine Learning Research (JMLR), vol. 13, (Jun. 2012), pp. 1809-1837.

Hidler, J. et al., "ZeroG: Overground gait and balance training system," Journal of Rehabilitation Research & Development, vol. 48, No. 4, Available as Early as Jan. 1, 2011, (2011), 12 pages.

Hines, M. L. et al., "The Neuron Simulation Environment," Neural Computation, vol. 9, No. 6, (Aug. 15, 1997), 26 pages.

Hofstoetter, U. S. et al., "Modification of Reflex Responses to Lumbar Posterior Root Stimulation by Motor Tasks in Healthy Subjects", Artificial Organs, vol. 32, No. 8, (2008), pp. 644-648.

Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.

Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.

Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.

Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.

Jarosiewicz, B. et al., "Supplementary Materials for Virtual typing by people with tetraplegia using a self-calibrating intracortical

(56)                References Cited

OTHER PUBLICATIONS brain-computer interface," Science Translational Medicine, vol. 7, No. 313, (Nov. 11, 2015), 26 pages.

Jarosiewicz, B. et al., "Virtual typing by people with tetraplegia using a self-calibrating intracortical brain-computer interface," Science Translational Medicine, vol. 7, No. 313, (Nov. 11, 2015), 11 pages.

Jilge, B. et al., "Initiating extension of the lower limbs in subjects with complete spinal cord injury by epidural lumbar cord stimulation", Exp Brain Res., vol. 154, (2004), pp. 308-326.

Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 22 pages.

Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.

Jones, D. R. et al., "Efficient Global Optimization of Expensive Black-Box Functions", Journal of Global Optimization, vol. 13, (1998), pp. 455-492.

Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.

Kirkwood, P., "Neuronal Control of Locomotion: "From Mollusc to Man", G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.

Kleinberg, R. et al., "Multi-armed bandits in metric spaces", In STOC, Computer and Automation Research Institute of the Hungarian Academy of Sciences, Budapest, Hungary, (2008), pp. 681-690.

Kocsis, L. et al. "Bandit Based Monte-Carlo Planning", European Conference on Machine Learning, Springer, Berlin, Heidelberg, (Sep. 2006), pp. 282-293.

Krassioukov, A. et al., "A Systematic Review of the Management of Autonomic Dysreflexia Following Spinal Cord Injury," Archives of Physical Medicine and Rehabilitation, vol. 90, No. 4, (Apr. 2009), 27 pages.

Krassioukov, A. et al., "A Systematic Review of the Management of Orthostatic Hypotension Following Spinal Cord Injury," Archives of Physical Medicine and Rehabilitation, vol. 90, No. 5, (May 2009), 22 pages.

Krause, A. et al., "Near-optimal Nonmyopic Value of Information in Graphical Models", In UAI, (2005), 8 pages.

Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.

Krause, A. et al. "Contextual Gaussian Process Bandit Optimization", In Advances in Neural Information Processing Systems (NIPS), (2011), 9 pages.

Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 17 pages.

Ladenbauer, J. et al., "Stimulation of the human lumbar spinal cord with implanted and surface electrodes: a computer simulation study", IEEE Transactions on Neural Systems and Rehabilitation Engineering, vol. 18, No. 6, (2010), pp. 637-645.

Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.

Liu, J. et al., "Stimulation of the Parapyramidal Region of the Neonatal Rat Brain Stem Produces Locomotor-Like Activity Involving Spinal 5-HT$_7$ and 5-HT$_{2A}$ Receptors", Journal of Neurophysiology, vol. 94, No. 2, Published Online May 4, 2005, (Aug. 1, 2005), 13 pages.

Lovely, R. et al., "Effects of Training on the Recovery of Full-Weight-Bearing Stepping in the Adult Spinal Cat," Experimental Neurology, vol. 92, No. 2, (May 1986), 15 pages.

Lozano, A. et al., "Probing and Regulating Dysfunctional Circuits Using Deep Brain Stimulation," Neuron, vol. 77, No. 3, (Feb. 6, 2013), 19 pages.

Lizotte, D. et al., "Automatic gait optimization with Gaussian process regression", In IJCAI, (2007), pp. 944-949.

McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.

Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.

Minassian, K. et al., "Peripheral and central afferent input to the lumbar cord", Biocybernetics and Biomedical Engineering, vol. 25, No. 3, (2005), pp. 11-29.

Minassian, K. et al., "Human lumbar cord circuitries can be activated by extrinsic tonic input to generate locomotor-like activity", Human Movement Science, vol. 26, No. 2, (2007), pp. 275-295.

Minassian, K. et al., "Posterior root-muscle reflex", Second Congress International Society of Intraoperative Neurophysiology (ISIN), Dubrovnik, Croatia, (2009), pp. 77-80.

Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286. 19, Abstract & Poster attached (2010), 1 page.

Minassian, K. et al., "Neuromodulation of lower limb motor control in restorative neurology", Clinical Neurology and Neurosurgery, vol. 114, (2012), pp. 489-497.

Minassian, K. et al., "Mechanisms of rhythm generation of the human lumbar spinal cord in repose to tonic stimulation without and with step-related sensory feedback", Biomed Tech., vol. 58, (Suppl. 1), (2013), 3 pages.

Minev, I. R. et al., "Electronic dura mater for long-term multimodal neural interfaces," Science Magazine, vol. 347, No. 6218, (Jan. 9, 2015), 64 pages.

Minoux, M., Accelerated greedy algorithms for maximizing submodular set functions. Optimization Techniques, LNCS, (1978), pp. 234-243.

Moraud, E. et al., "Mechanisms Underlying the Neuromodulation of Spinal Circuits for Correcting Gait and Balance Deficits after Spinal Cord Injury," Neuron, vol. 89, No. 4, Published Online Feb. 4, 2016, (Feb. 17, 2016), 15 pages.

Murg, M. et al., "Epidural electric stimulation of posterior structures of the human lumbar spinal cord: 1. Muscle twitches—a functional method to define the site of stimulation", Spinal Cord, vol. 38, (2000), pp. 394-402.

Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.

Musienko, P. et al., "Controlling specific locomotor behaviors through multidimensional monoaminergic modulation of spinal circuitries," The Journal of Neuroscience, vol. 31, No. 25, (Jun. 22, 2011), 32 pages.

Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.

Nandra, M. S. et al., "A parylene-based microelectrode array implant for spinal cord stimulation in rats", Conference Proceedings IEEE Eng. Med. Biol. Soc., (2011), pp. 1007-1010.

(56) References Cited

OTHER PUBLICATIONS

Nandra, M. S. et al., "A wireless microelectrode implant for spinal cord stimulation and recording in rats", Presentation Abstract, 2013.

Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.

Pearson, K. G., "Generating the walking gait: role of sensory feedback," Progress in Brain Research, vol. 143, Chapter 12, Published Online Nov. 28, 2003, (2004), 7 pages.

Phillips, A. et al., "Perturbed and spontaneous regional cerebral blood flow responses to changes in blood pressure secondary high-level spinal cord injury: the effect of midodrine," Journal of Applied Physiology, vol. 116, No. 6, Available Online Jan. 16, 2014, (Mar. 15, 2014), 20 pages.

Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, (May 2014), 8 pages.

Phillips, A. A. et al., "Contemporary Cardiovascular Concerns after Spinal Cord Injury: Mechanisms, Maladaptations, and Management," Journal of Neurotrama, vol. 32, No. 24, (Dec. 15, 2015), 17 pages.

Pratt, G. et al., "Stiffness Isn't Everything," Proceedings of the Fourth International Symposium on Experimental Robotics, (Jun. 30, 1995), 6 pages.

Pratt, J. et al., "Series elastic actuators for high fidelity force control," Industrial Robot: An International Journal, vol. 29, No. 3, Available as Early as Jan. 1, 2002, (1995), 13 pages.

Prochazka, A. et al., "Ensemble firing of muscle afferents recorded during normal locomotion in cats," The Journal of Physiology, vol. 507, No. 1, (Feb. 15, 1998), 12 pages.

Prochazka, A. et al., "Models of ensemble filing of muscle spindle afferents recorded during normal locomotion in cats," The Journal of Physiology, vol. 507, No. 1, (Feb. 15, 1998), 15 pages.

Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.

Rasmussen, C. E. et al., "Gaussian Processes for Machine Learning", The MIT Press, Cambridge, Massachusetts, (2006), 266 pages.

Rasmussen, C. E. et al., "Gaussian Processes for Machine Learning (GPML) Toolbox", The Journal of Machine Learning Research, vol. 11, (2010), pp. 3011-3015.

Rattay, F. et al., "Epidural electrical stimulation of posterior structures of the human lumbosacral cord: 2. Quantitative analysis by computer modeling", Spinal Cord, vol. 38, (2000), pp. 473-489.

Reinkensmeyer, D. et al., "Tools for understanding and optimizing robotic gait training", Journal of Rehabilitation Research & Development, vol. 43, No. 5, (Aug. 2006), 14 pages.

Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.

Robbins, H., "Some Aspects of the Sequential Design of Experiments", Bull. Amer. Math. Soc., vol. 58, (1952), pp. 527-535.

Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.

Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.

Ryzhov, I. O. et al., "The knowledge gradient algorithm for a general class of online learning problems", Operations Research, vol. 60, No. 1, (2012), pp. 180-195.

Sayenko, D. et al., "Neuromodulation of evoked muscle potentials induced by epidural spinal- cord stimulation in paralyzed individuals," Journal of Neurophysiology, vol. 111, No. 5, Published Online Dec. 11, 2013, (2014), 12 pages.

Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.

Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.

Stienen, A. H. A. et al., "Analysis of reflex modulation with a biologically realistic neural network," Journal of Computer Neuroscience, vol. 23, No. 3, Available Online May 15, 2007, (Dec. 2007), 16 pages.

Sun, F. et al., "Sustained axon regeneration induced by co-deletion of PTEN and SOCS3" Nature, vol. 480, No. 7377, Published Online Nov. 6, 2011, (Dec. 15, 2011), 12 pages.

Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.

Tenne, Y. et al., "Computational Intelligence in Expensive Optimization Problems", vol. 2 of Adaptation, Learning, and Optimization, Springer, Berlin Heidelberg, (2010), pp. 131-162.

Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.

Vallery, H. et al., "Compliant Actuation of Rehabilitation Robots," IEEE Robotics & Automation Magazine, vol. 15, No. 3, (Sep. 12, 2008), 10 pages.

Van Den Brand, R. et al., "Restoring Voluntary Control of Locomotion after Paralyzing Spinal Cord Injury," Science Magazine, vol. 336, No. 6085, (Jun. 1, 2012), 5 pages.

Ward, A. R., "Electrical Stimulation Using Kilohertz-Frequency Alternating Current", Physical Therapy, vol. 89, Published online Dec. 18, 2008, (2009), pp. 181-190.

Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.

Wenger, N. et al. "Closed-loop neuromodulation of spinal sensorimotor circuits controls refined locomotion after complete spinal cord injury", Sci Transl Med., Sep. 24, 2014, vol. 6, Issue 255, (2014), 10 pages.

Wenger, N. et al., "Spatiotemporal neuromodulation therapies engaging muscle synergies improve motor control after spinal cord injury," Natural Medicine, vol. 22, No. 2, Available Online Jan. 18, 2016, (Feb. 2016) 33 pages.

Wernig, A. et al., "Laufband locomotion with body weight support improved walking in persons with severe spinal cord injuries", Paraplegia, vol. 30, No. 4, (Apr. 1992), 10 pages.

Wernig, A., "Ineffectiveness• of Automated Locomotor Training," Archives of Physical Medicine and Rehabilitation, vol. 86, No. 12, (Dec. 2005), 2 pages.

Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.

Widmer, C. et al., Inferring latent task structure for multitask learning by multiple kernel learning, BMC Bioinformatics, vol. 11, (Suppl 8:S5), (2010), 8 pages.

Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.

Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.

(56)　　　　　References Cited

OTHER PUBLICATIONS

Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.

Zhang, T. C. et al., "Mechanisms and models of spinal cord stimulation for the treatment of neuropathic pain," Brain Research, vol. 1569, Published Online May 4, 2014, (Jun. 20, 2014), 13 pages.

Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.

Communication Pursuant to Article 94(3) EPC in counterpart European Application No. 19209911.7, dated Jul. 20, 2023, (5 pages).

Ateh, D. D. et al., "Polypyrrole-based Conducting Polymers and Interactions with Biological Tissues", Journal of the Royal Society Interface, vol. 3, (Jun. 22, 2006), pp. 741-752.

Axisa, F. et al., "Elastic and Conformable Electronic Circuits and Assemblies using MID in polymer", 6th International Conference on Polymers and Adhesives in Microelectronics and Photonics, IEEE Polytronic 2007 Conference, (Jan. 1, 2007), pp. 280-286.

Bizzi, E. et al., "Modular Organization of Motor Behavior", Trends in Neurosciences, vol. 18, No. 10, (Oct. 1995), 8 pages.

Capogrosso, M. et al., "A Brain-Spinal Interface Alleviating Gait Deficits after Spinal Cord Injury in Primates", Nature, vol. 539, No. 7628, (Nov. 10, 2016), 39 pages.

Chatagny, P. et al., "Distinction between hand dominance and hand preference in primates: a behavioral investigation of manual dexterity in nonhuman primates (macaques) and human subjects", Brain and Behavior, vol. 3, No. 5, (Sep. 2013), 21 pages.

Communication Pursuant to Article 94(3) EPC in related European Patent Application No. 20160841.1 mailed Mar. 6, 2024, 5 pages.

Communication Pursuant to Article 94(3) EPC in related European Patent Application No. 21660801.7 mailed Mar. 7, 2024, 6 pages.

Communication Pursuant to Article 94(3) EPC in related European Patent Application No. 20726108.2 mailed Mar. 20, 2024, 4 pages.

Communication Regarding Extended European Search Report in related European Patent Application No. 19211738.0 mailed May 27, 2020, 8 pages.

Communication Regarding Extended European Search Report in related European Patent Application No. 18173218.1 mailed Jan. 7, 2019, 6 pages.

Communication Regarding Extended European Search Report in related European Patent Application No. 23189900.6 mailed Jan. 15, 2024, 7 pages.

Communication Regarding Extended European Search Report in related European Patent Application No. 19211738.0 mailed May 20, 2020, 8 pages.

Communication Regarding Extended European Search Report in related European Patent Application No. 24153829.7 mailed May 22, 2024, 8 pages.

Communication Regarding Extended European Search Report in related European Patent Application No. 20020190.3 mailed Oct. 5, 2020, 7 pages.

Cotton, D. P. J. et al.: "A Multifunctional Capacitive Sensor for Stretchable Electronic Skins", IEEE Sensors Journal, IEEE Service Center, New York, NY, US, vol. 9, No. 12, (Dec. 1, 2009), pp. 2008-2009.

Cyganowski, A. et al., "Stretchable electrodes for neuroprosthetic interfaces," Sensors, 2012 IEEE, Taipei, (2012), pp. 1-4.

Dominici, N. et al., "Versatile robotic interface to evaluate, enable and train locomotion and balance after neuromotor disorders", Nature Medicine, vol. 18, No. 7, Jul. 2012, Published Online May 31, 2012, 8 pages.

Dunne, L. et al., "Initial development and testing of a novel foam-based pressure sensor for wearable sensing," Journal of NeuroEngineering and Rehabilitation, vol. 2, No. 4, (2005), 7 pages.

Feng, G. H. et al., "Universal concept for fabricating micron to millimeter sized 3-D parylene structures on rigid and flexible substrates," in Proc. IEEE 15th Internal Conference on Micro Electro Mechanical System, Kyoto, Japan, (2003), pp. 594-597.

Gerasimenko, Y. et al., "Spinal cord reflexes induced by epidural spinal cord stimulation in normal awake rats", Journal of Neuroscience Methods, vol. 157, No. 2, (Oct. 30, 2006), 11 pages.

Graf, N. et al., "Electrochemically Stimulated Release from Liposomes Embedded in a Polyelectrolyte Multilayer", Advanced Functional Materials, vol. 21, (2011), pp. 1666-1672.

Graz, I. et al., "Flexible ferroelectret field-effect transistor for large-area sensor skins and microphones," Applied Physics Letters, American Institute of Physics, vol. 89, No. 7, (2006), pp. 73501-1-73501-3.

Graz, I. et al., "Silicone substrate within situ strain relief for stretchable thin-film transistors", Applied Physics Letters, AIP, American Institute of Physics, vol. 98, No. 12, (Mar. 22, 2011), pp. 124101-124101.

Harkema, S. et al., "Normalization of Blood Pressure with Spinal Cord Epidural Stimulation After Severe Spinal Cord Injury", Frontiers in Human Neuroscience, (Mar. 8, 2018), 11 pages.

International Search Report and Written Opinion issued in related PCT Application No. EP2017/083478, mailed May 3, 2018, 10 pages.

International Search Report and Written Opinion issued in related PCT Application No. EP2018/082942, mailed Feb. 14, 2019, 12 pages.

International Search Report and Written Opinion issued in related PCT Application No. EP2020/063563, mailed Jul. 30, 2020, 14 pages.

International Search Report and Written Opinion issued in related PCT Application No. EP2020/063564, mailed Sep. 11, 2020, 14 pages.

Jenny, A. et al., "Principles of Motor Organization of the Monkey Cervical Spinal Cord", The Journal of Neuroscience, vol. 3, No. 4, Mar. 1983, 9 pages.

Kim, W. S. et al., "Ultra-sensitive Flexible Pressure Sensor with Stamped Polyurethane Rubber," 2011 11th IEEE Conference on Nanotechnology, (2011), pp. 1607-1610.

Lacour, S. et al., "Flexible and stretchable micro-electrodes for in vitro and in vivo neural interfaces", Med. Biol. Eng. Comput., vol. 48, (2010), pp. 945-954.

Lacour, S. et al., "Stretchable gold conductors on elastomeric substrates", Applied Physics Letters, vol. 82, No. 15, (Apr. 14, 2003), pp. 2404-2406.

Levine, A. et al., "Identification of cellular node for motor control pathways", Nature Neuroscience, vol. 17, No. 4, Apr. 2024, Available Online Mar. 9, 2014, 22 pages.

Meacham, K. W. et al., "A lithographically-patterned, elastic multielectrode array for surface stimulation of the spinal cord," Biomed Microdevices, vol. 10, (2008), pp. 259-269.

Metzger, C. et al., "Flexible-foam-based capacitive sensor arrays for object detection at law cost," Applied Physics Letters, American Institute of Physics, vol. 92, No. 1, (2008), pp. 13506-1-13506-3.

Minev, I. R. et al., "Evaluation of an Elastomer Based Gold Microelectrode Array for Neural Recording Applications," Proceedings of the 5th International IEEE/EMBS Conference on Neural Engineering, Cancun, Mexico, (Apr. 27-May 1, 2011), pp. 482-485.

Minev, I. R. et al., "High sensitivity recording of afferent nerve activity using ultra-compliant microchannel electrodes: an acute in vivo validation," J. Neural Eng., (2012), vol. 9, No. 1-7.

Oxford English Dictionary Definition of "Inserted" (Year: 2020), 2 pages.

Park, K. J. et al., "Continuous "Over and Over" Suture for Tricuspid Ring Annuloplasty", Korean Journal of Thoracic and Cardiovascular Surgery, vol. 45, (2012), pp. 19-23.

Pellinen, D. S. et al., "Multifunctional Flexible Parylene-Based Intracortical Microelectrodes", Proceedings of the 2005 IEEE: Engineering in Medicine and Biology 27th Annual Conference, (Sep. 1-4, 2005), pp. 5272-5275.

Pflug, H. et al., "Parallel Resonant Inductive Wireless Power Transfer", IEEE, Proceedings of Wireless Power Week 2019, London, United Kingdom (Jun. 17, 2019), pp. 182-187.

Rasmussen, C. E. "Gaussian Processes in Machine Learning", L.N.A.I., vol. 3176, (2003) pp. 63-71.

Robinson, A. et al., "Hybrid stretchable circuits on silicone substrate," Journal of Applied Physics, vol. 11, No. 5, (2014), 5 pages.

(56) References Cited

OTHER PUBLICATIONS

Schmidlin, E. et al., "Behavioral Assessment of Manual Dexterity in Non-Human Primates", Journal of Visualized Experiments, vol. 57, No. e3258, Nov. 11, 2011, 11 pages.

Sherman, J. et al., "Measurements of the normal cervical spinal cord on MR Imaging", American Journal of Neuroradiology, vol. 11, No. 2, Mar. 1990, 4 pages.

Srinivas, N. et al., "Gaussian process optimization in the bandit setting: No regret and experimental design", In Proceedings of the 27th International Conference on Machine Learning, (2010), 17 pages.

Suzuki, T. et al., "A 3D flexible parylene probe array for multi-channel neural recording", IEEE Neural Eng., (2003), pp. 154-156.

Takeuchi, S. et al., "3D flexible multichannel neural probe array", J. Micromech. Microeng., vol. 14, No. 104-107, (2004), 4 pages.

Wan, D. et al., "Life-threatening outcomes associated with autonomic dysreflexia: A clinical review," Journal of Spinal Cord Medicine, vol. 37, No. 1, (Jan. 2014), 9 pages.

Wei, P. et al., "Stretchable microelectrode array using room-temperature liquid alloy interconnects", Journal of Micromechanics and Microengineering, vol. 21, No. 054015, (2011), pp. 1-8.

European Examination Report in counterpart European Patent Application No. 17826212.7 mailed Dec. 21, 2020, 7 pages.

European Opposition filed in counterpart European Patent Application No. 17826212.7 on Dec. 2, 2022, 56 pages.

"Health Journalism Glossary: Bidirectional", Association of Health Care Journalists (AHCJ), 2024, 3 pages.

Hohenschurz-Schmidt, D. J. et al., Linking Pain Sensation to the Autonomic Nervous System: The Role of the Anterior Cingulate and Periaqueductal Gray Resting—State Networks, Front Neuroscience, Feb. 27, 2020, vol. 14, No. 147, 15 pages.

Andersson, K.-E. et al., "CNS Involvement in Overactive Bladder—Pathophysiology and Opportunities for Pharmacological Intervention", Drugs, vol. 63, No. 23, (2003), pp. 2595-2611.

Augustine, G. J. et al., "Autonomic Regulation of the Bladder", Neuroscience, $2^{nd}$ edition, Chapter Twenty-One, Sunderland, (MA), Dec. 4, 2022, 5 pages.

Coursera, (n.d.), What is Machine Learning? Definition, Types, and Examples. Coursera. https://www.coursera.org/articles/what-is-machine-learning, (Year: 2023), 12 pages.

Danner, S. M. et al., "Can the Human Lumbar Posterior Columns be Stimulated by Transcutaneous Spinal Cord Stimulation? A modeling study", Europe PMC funders author manuscripts, Artificial Organs, (2011), vol. 35, No. 3, pp. 257-262.

Desantana, J. M. et al., "Effectiveness of Transcutaneous Electrical Nerve Stimulation for Treatment of Hyperalgesia and Pain", Curr Rheumatol Rep., (2008), vol. 10, pp. 492-499.

Drummond, G. B. et al., "Thoracic impedance used for measuring chest wall movement in postoperative patients", British Journal of Anaesthesia, (1996), vol. 77, pp. 327-332.

Dubinsky, R. M. et al., "Assessment: Efficacy of transcutaneous electric nerve stimulation in the treatment of pain in neurologic disorders (an evidenced-based review)", Report of the Therapeutics and Technology Assessment Subcommittee of the American Academy of Neurology, Neurology, (2010), vol. 74, pp. 173-176.

Edgerton, V. R. et al., "Epidural stimulation of the spinal cord in spinal cord injury: current status and future challenges", Expert Rev. Neurother, doi: 10.1586/ern.11.129 [NIH Public Access—Author Manuscript—5 pages], (Oct. 2011), vol. 11, No. 10, pp. 1351-1353.

European Office Action and Annex issued in counterpart European Patent Application No. 18807366.2 mailed Mar. 22, 2023, European Patent Office, Munich, Germany, 4 pages.

EPO Communication and Supplementary European Search Report issued in counterpart European Patent Application No. 17745012.9 mailed Aug. 3, 2019, pp. 1-8.

Gerasimenko, Y. et al., "Novel and Direct Access to the Human Locomotor Spinal Circuitry", Journal of Neuroscience, (Mar. 10, 2010), vol. 30, No. 10, pp. 3700-3708.

Gerasimenko, Y. P. et al., "Epidural Spinal Cord Stimulation Plus Quipazine Administration Enable Stepping Complete Spinal Adult Rats", J. Neurophysiol., (2007), vol. 98, pp. 2525-2536.

Gerasimenko, Y. et al., "Initiation and modulation of locomotor circuitry output with multisite transcutaneous electrical stimulation of the spinal cord in noninjured humans", J. Neurophysiol., (2015), vol. 113, pp. 834-842.

Gerasimenko, Y. et al., "Transcutaneous electrical spinal-cord stimulation in humans", Ann Phys Rehabil. Med., (2015), vol. 58, No. 4, pp. 225-231.

Giuliano, F. et al. "Neural Control of Erection", Physiology & Behavior, vol. 83, No. 2, (Nov. 15, 2004), pp. 189-201.

Hovey, C. et al., "The New Guide to Magnet Stimulation", The Magstim Company Ltd., (Jul. 21, 2006), 45 pages.

International Search Report and Written Opinion issued in related PCT Application No. PCT/US2017/015435, mailed May 8, 2017, 9 pages.

International Search Report and Written Opinion issued in related PCT Application No. PCT/EP2020/053381, mailed May 12, 2020, 8 pages.

International Search Report and Written Opinion issued in related PCT Application No. PCT/EP2018/082939, mailed Feb. 14, 2019, 11 pages.

Iyer, P. C. et al., "Characterization of stimulus response curves obtained with transcranial magnetic stimulation from bilateral tibialis anterior muscles post stroke", Neuroscience Letters, vol. 713, (2019), pp. 134530.

Jaman, R., (2022), A retrospective cross-sectional survey of lumbosacral recorded at the D.U.T. Chiropractic Day Clinic (1995-2005), https://doi.org/10.51415/10321/221, (Year: 2014), 94 pages.

Krenn, M. et al., "Selectivity of transcutaneous stimulation of lumbar posterior roots at different spinal levels in humans.", Biomed Tech (2013), 58 (Suppl. 1), DOI 10.1515/bmt-2013-4010, 2 pages.

Ichiyama, R. M. et al., "Hindlimb stepping movements in complete spinal rats induced by epidural spinal cord stimulation", Neuroscience Letters, (2005), vol. 383, pp. 339-344.

Kapetanakis, S. et al., "*Cauda Equina* Syndrome Due to Lumbar Disc Herniation: a Review of Literature", Folia Medica, (Dec. 22, 2017), vol. 59, No. 4, pp. 377-386.

Kirazli, O. et al., "Anatomy of the spinal dorsal root entry zone: its clinical significance", Acta Neurochir, vol. 156, (2014), pp. 2351-2358.

Kitano, K. et al., "Spinal reflex in human lower leg muscles evolved by transcutaneous spinal cord stimulation", Journal of Neuroscience Methods, (2009), vol. 180, pp. 111-115.

Kondo, et al., "Laser monitoring of chest wall displacement", Eur. Respir. J., (1997), vol. 10, pp. 1865-1869.

Lu, D. et al., "Engaging cervical spinal cord networks to re-enable volitional control of hand function in tetraplegic patients", Neurorehabilitation and Neural Repair, vol. 30, No. 10, Available Online May 18, 2016, Nov. 2016, 21 pages.

Minassian, K. et al., "Transcutaneous spinal cord stimulation", International Society for Restoration Neurology, (Aug. 2011), 6 pages.

Minassian, K. et al. "Posterior root-muscle reflexes elicited by transcutaneous stimulation of the human lumbosacral cord", Muscle and Nerve, (Mar. 2007), vol. 35, pp. 327-336.

Nandra, M. et al., "Microelectrode Implants for Spinal Cord Stimulation in Rats", Doctor of Philosophy Thesis, California Institute of Technology, (2014), 104 pages.

Needle, A. R. et al., "Brain Regulation of muscle tone in healthy and functionally unstable ankles", Journal of Sport Rehabilitation, (2013), vol. 22, No. 1, pp. 202-211.

Niu, T. et al., "A Proof-of-Concept Study of Transcutaneous Magnetic Spinal Cord Stimulation for Neurogenic Bladder", Scientific Reports, (2018), vol. 8, 12549, (12 pages).

[No Author], National Health Service, "Lumbar Decompression Surgery: When it's used", NHS, Apr. 28, 2022, https://www.nhs.uk/conditions/lumbar-decompression-surgery/why-its-done/#:-:text=Cauda%equina%20syndrome%20is%20a,is%20sever%20or%20getting%20worse, 2 pages.

(56) References Cited

OTHER PUBLICATIONS

[No Author], Vital Signs—Cleveland Clinic [Retrieved on Nov. 22, 2021], Retrieved from the Internet: URL: https://my.clevelandclinic.org/health/articles/10881-vital-signs, 7 pages.

Roy, F. D. et al., "Effect of percutaneous stimulation at different spinal levels on the activation of sensory and motor roots", Exp. Brain Res., (2012), vol. 223, pp. 281-289.

Sayenko, D. G. et al., "Spinal segment-specific transcutaneous stimulation differentially shapes activation pattern among motor pools in humans", (2015), J. Appl. Physiol., vol. 118, pp. 1364-1374.

Seifert, H. M. et al., "Restoration of Movement Using Functional Electrical Stimulation and Bayes' Theorem", The Journal of Neuroscience, (Nov. 1, 2022), vol. 22, No. 21, pp. 9465-9474.

Shafik, A. et al., "Magnetic stimulation of the cavernous nerve for the treatment of erectile dysfunction in humans", International Journal of Impotence Research, (2000), vol. 12, pp. 137-142.

Shafik, A. et al., "Extrapelvic cavernous nerve stimulation in erectile dysfunction. Human Study", Andrologia, (1996), vol. 28, No. 3, pp. 151-156. Doi: 10.1111/j. 1439-0272. 1996.tb02774.x [Abstract—2 pages].

Sharpe, A. et al., "Upper-limb muscles responses to epidural, subdural and intraspinal stimulation of the cervical spinal cord", Journal of Neural Engineering, vol. 11, No. 1, Feb. 2014, 16 pages.

Szava, Z. et al., "Transcutaneous electrical spinal cord stimulation: Biophysics of a new rehabilitation method after spinal cord injury", (Jan. 2011), ISBN: 978-3-639-34154-6, 95 pages.

Tanabe, S. et al., "Effects of transcutaneous electrical stimulation combined with locomotion-like movement in the treatment of post-stroke gait disorder: a single-case study", (2008), vol. 30, No. 5, 411-416 Abstract, 1 page.

Temel, Y. et al., "Case Report—Deep brain stimulation of the thalamus can influence penile erection", International Journal of Impotence Research, vol. 16, pp. 91-94.

Troni, W. et al., "A methodological reappraisal of non invasive high voltage electrical stimulation of lumbosacral nerve roots", Clin. Neurophysiol., (2011), vol. 122, pp. 2071-2080.

Wang, T. et al., "Incidence of C5 nerve root palsy after cervical surgery—A meta-analysis for decade", Medicine, (2017), vol. 96, No. 45, 14 pages.

Gerasimenko, Y. P. et al., "Epidural Spinal Cord Stimulation Plus Quipazine Administration Enable Stepping Complete Spinal Adult Rats", Journal of Neurophysiology, (2007), vol. 98, No. 5, pp. 2525-2536.

Ginsbourger, D. et al., "Kriging is well-suited to parallelize optimization", Computational Intelligence in Expensive Optimization Problems, Berlin, Heidelberg: Springer Berlin Heidelberg, (2010), Ch. 6, pp. 131-162.

Giuliano, F. et al., "Neural Control of Erection", Physiology & Behavior, (2004), vol. 83, No. 2, pp. 189-201.

Hofstoetter, U. S. et al., "Modification of spasticity by transcutaneous spinal cord stimulation in individuals with incomplete spinal cord injury", The Journal of Spinal Cord Medicine, (2014), vol. 37, No. 2, pp. 202-211.

Hovey, C. et al., "The New Guide to Magnet Stimulation", The Magstim Company Ltd., (2006), pp. 1-45.

Hung, C. C. et al., "Transparent microprobe array fabricated by MEMS hot embossing technology for photodynamic therapy application", IEICE Electronics Express, (2010), vol. 7, No. 9, pp. 569-576.

Ichiyama, R. M. et al., "Hindlimb stepping movements in complete spinal rats induced by epidural spinal cord stimulation", Neuroscience Letters, (2005), vol. 383, No. 3, pp. 339-344.

International Search Report and Written Opinion issued in counterpart PCT Application No. PCT/EP2018/082939, mailed Feb. 14, 2019, 11 pages.

International Search Report and Written Opinion issued in counterpart PCT Application No. PCT/EP2020/053381, mailed May 12, 2020, 8 pages.

International Search Report and Written Opinion issued in counterpart PCT Application No. PCT/US2012/064878 mailed Mar. 19, 2013, 11 pages.

International Search Report and Written Opinion issued in counterpart PCT Application No. PCT/US2014/029340 mailed Aug. 6, 2014, 11 pages.

International Search Report and Written Opinion issued in counterpart PCT Application No. PCT/US2014/057886 mailed Dec. 24, 2014, 6 pages.

International Search Report and Written Opinion issued in counterpart PCT Application No. PCT/US2015/011263 mailed May 19, 2015, 12 pages.

International Search Report and Written Opinion issued in counterpart PCT Application No. PCT/US2015/046378 mailed Dec. 1, 2015, 5 pages.

International Search Report and Written Opinion issued in counterpart PCT Application No. PCT/US2015/047268 mailed Dec. 8, 2015, 17 pages.

International Search Report and Written Opinion issued in counterpart PCT Application No. PCT/US2015/047272 mailed Dec. 3, 2015, 11 pages.

International Search Report and Written Opinion issued in counterpart PCT Application No. PCT/US2016/041802 mailed Sep. 12, 2016, 17 pages.

International Search Report and Written Opinion issued in counterpart PCT Application No. PCT/US2016/045898 mailed Dec. 5, 2016, 13 pages.

International Search Report and Written Opinion issued in counterpart PCT Application No. PCT/US2016/049129 mailed Dec. 5, 2016, 13 pages.

International Search Report and Written Opinion issued in counterpart PCT Application No. PCT/US2017/015435, mailed May 8, 2017, 9 pages.

International Search Report and Written Opinion issued in counterpart PCT Application No. PCT/US2018/015098 mailed Mar. 12, 2018, 9 pages.

International Search Report and Written Opinion issued in counterpart PCT Application No. PCT/US2018/033942 mailed Aug. 31, 2018, 8 pages.

International Search Report and Written Opinion issued in counterpart PCT Application No. PCT/US2019/047551 mailed Nov. 21, 2019, 9 pages.

International Search Report and Written Opinion issued in counterpart PCT Application No. PCT/US2019/047777 mailed Nov. 14, 2019, 15 pages.

International Search Report and Written Opinion issued in counterpart PCT Application No. PCT/US2020/033830 mailed Oct. 14, 2020, 10 pages.

International Search Report and Written Opinion issued in counterpart PCT Application No. PCT/US2022/024673 mailed Jun. 28, 2022, 8 pages.

International Search Report issued in counterpart PCT Application No. PCT/US2012/020112 mailed Jul. 30, 2012, 4 pages.

International Search Report issued in counterpart PCT Application No. PCT/US2012/022257 mailed Sep. 3, 2012, 4 pages.

International Search Report issued in counterpart PCT Application No. PCT/US2012/030624 mailed Oct. 31, 2012, 3 pages.

International Search Report issued in counterpart PCT Application No. PCT/US2012/064874 mailed Mar. 19, 2013, 4 pages.

Iyer, P. C. et al., "Characterization of stimulus response curves obtained with transcranial magnetic stimulation from bilateral tibialis anterior muscles post stroke", Neuroscience Letters, (2019), vol. 713, pp. 1-15.

Jaman, R., "A retrospective cross-sectional survey of lumbo-sacral recorded at the D.U.T. Chiropractic Day Clinic (1995-2005)", (2014). Durban University of Technology, Master's Degree in Technology dissertation. Retrieved from the Internet: <URL: https://doi.org/10.51415/10321/221>, 94 pages.

Jonic, S. et al., "Three machine learning techniques for automatic determination of rules to control locomotion", IEEE Transactions on Biomedical Engineering, (1999), vol. 46, No. 3, pp. 300-310.

(56) References Cited

OTHER PUBLICATIONS

Kapetanakis, S. et al., "Cauda Equina Syndrome Due to Lumbar Disc Herniation: a Review of Literature", Folia Medica, (2017), vol. 59, No. 4, pp. 377-386.

Kim, Y. et al., "Electrical behavior of defibrillation and pacing electrodes", Proceedings of the IEEE, (2002), vol. 84, No. 3, pp. 446-456.

Kirazh, O. et al., "Anatomy of the spinal dorsal root entry zone: its clinical significance", Acta Neurochirurgica, (2014), vol. 156, pp. 2351-2358.

Kitano, K. et al., "Spinal reflex in human lower leg muscles evolved by transcutaneous spinal cord stimulation", Journal of Neuroscience Methods, (2009), vol. 180, No. 1, pp. 111-115.

Kondo, T. et al., "Laser monitoring of chest wall displacement", European Respiratory Journal, (1997), vol. 10, No. 8, pp. 1865-1869.

Krenn, M. et al., "Selectivity of transcutaneous stimulation of lumbar posterior roots at different spinal levels in humans", Biomedical Technology, (2013), vol. 58 (Suppl. 1), pp. 1-2.

Lu, D. et al., "Engaging cervical spinal cord networks to re-enable volitional control of hand function in tetraplegic patients", Neurorehabilitation and Neural Repair, (2016), vol. 30, No. 10, pp. 951-962.

Minassian, K. et al., "Human Lumbar Cord Model of the Locomotor Central Pattern Generator", Second Congress International Society of Intraoperative Neurophysiology (ISIN), (2009), pp. 11-13.

Minassian, K. et al., "Neurophysiology of the human lumbar locomotor pattern generator", Proceedings 10th Vienna International Workshop on Functional Electrical Stimulation, Center for Medical Physics and Biomedical Engineering, (2010), pp. 259-261.

Minassian, K. et al., "Posterior root-muscle reflexes elicited by transcutaneous stimulation of the human lumbosacral cord", Muscle and Nerve, (2007), vol. 35, No. 3, pp. 327-336.

Minassian, K. et al., "Transcutaneous spinal cord stimulation", International Society for Restoration Neurology, (2011), pp. 1-6.

Nandra, M. et al., "Microelectrode Implants for Spinal Cord Stimulation in Rats", Doctor of Philosophy Thesis, California Institute of Technology, (2014), pp. 1-104.

Needle, A. R. et al., "Brain Regulation of muscle tone in healthy and functionally unstable ankles", Journal of Sport Rehabilitation, (2013), vol. 22, No. 3, pp. 202-211.

Niu, T. et al., "A Proof-of-Concept Study of Transcutaneous Magnetic Spinal Cord Stimulation for Neurogenic Bladder", Scientific Reports, (2018), vol. 8, No. 1, pp. 1-12.

PeachPit, "Working with Basic Shapes in Adobe Illustrator CC (2014 release)," PeachPit, Nov. 3, 2014 [retrieved on Feb. 6, 2024]. Retrieved from the Internet: <URL: https://www.peachpit.com/articles/article.aspx?p=2253413&seqNum=3>.

Purves, D. et al., "Autonomic Regulation of the Bladder", Neuroscience, 2nd edition, Chapter Twenty-One, Sunderland, (MA), (2022), pp. 1-5.

Roy, F. D. et al., "Effect of percutaneous stimulation at different spinal levels on the activation of sensory and motor roots", Experimental Brain Research, (2012), vol. 223, pp. 281-289.

Rubinstein et al., "Current Density Profiles of Surface Mounted and Recessed Electrodes for Neural Prostheses", Biomedical Engineering, IEEE Transactions on BME, (1987), vol. 34, No. 11, pp. 864-875.

Sayenko, D. et al., "Neuromodulation of evoked muscle potentials induced by epidural spinal-cord stimulation in paralyzed individuals", Journal of Neurophysiology, (2014), vol. 111, No. 5, pp. 1088-1099.

Sayenko, D. G. et al., "Spinal segment-specific transcutaneous stimulation differentially shapes activation pattern among motor pools in humans", Journal of Applied Physiology, (2015), vol. 118, No. 11, pp. 1364-1374.

Seifert, H. M. et al., "Restoration of Movement Using Functional Electrical Stimulation and Bayes' Theorem", The Journal of Neuroscience, (2002), vol. 22, No. 21, pp. 9465-9474.

Shafik, A. et al., "Extrapelvic cavernous nerve stimulation in erectile dysfunction. Human Study", Andrologia, (1996), vol. 28, No. 3, pp. 151-156.

Shafik, A. et al., "Magnetic stimulation of the cavernous nerve for the treatment of erectile dysfunction in humans", International Journal of Impotence Research, (2000), vol. 12, No. 3, pp. 137-141.

Sharpe, A. et al., "Upper-limb muscles responses to epidural, subdural and intraspinal stimulation of the cervical spinal cord", Journal of Neural Engineering, (2014), vol. 11, No. 1, pp. 1-16.

Srinivas, N. et al., "Gaussian process optimization in the bandit setting: No regret and experimental design", In Proceedings of the 27th International Conference on Machine Learning, (2010), pp. 1-17.

Szava, Z. et al., "Transcutaneous electrical spinal cord stimulation: Biophysics of a new rehabilitation method after spinal cord injury", VDM Publishing, Saarbrucken, Germany, (2011), pp. 1-95.

Tanabe, S. et al., "Effects of transcutaneous electrical stimulation combined with locomotion-like movement in the treatment of post-stroke gait disorder: a single-case study", (2008), vol. 30, No. 5, pp. 411-416.

Temel, Y. et al., "Case Report—Deep brain stimulation of the thalamus can influence penile erection", International Journal of Impotence Research, (2004), vol. 16, No. 1, pp. 91-94.

Troni, W. et al., "A methodological reappraisal of non invasive high voltage electrical stimulation of lumbosacral nerve roots", Clinical Neurophysiology, (2011), vol. 122, No. 10, pp. 2071-2080.

Tungjitkusolmun, S. et al., "Finite element analyses of uniform current density electrodes for radio-frequency cardiac ablation", IEEE Transactions on Biomedical Engineering, (2000), vol. 47, No. 1, pp. 32-40.

Valchinov, E. S. et al., "An active electrode for biopotential recording from small localized bio-sources", BioMedical Engineering OnLine, (2004), vol. 3, No. 25, pp. 1-14.

Wang, J. M. et al., "Gaussian process dynamical models for human motion", IEEE Transactions on Pattern Analysis and Machine Intelligence, (2007), vol. 30, No. 2, pp. 283-298.

Wang, T. et al., "Incidence of C5 nerve root palsy after cervical surgery—A meta-analysis for decade", Medicine, (2017), vol. 96, No. 45, pp. 1-14.

Ward, A. R. et al., "Sensory, motor, and pain thresholds for stimulation with medium frequency alternating current", Archives of Physical Medicine and Rehabilitation, (1998), vol. 79, No. 3, pp. 273-278.

Wenger, N. et al., "Closed-loop neuromodulation of spinal sensorimotor circuits controls refined locomotion after complete spinal cord injury", Science Translational Medicine, (2014), vol. 6, Issue 255, pp. 1-11.

Wiley, J. D. et al., "Analysis and Control of the Current Distribution under Circular Dispersive Electrodes", Biomedical Engineering, IEEE Transactions on BME, (1982), vol. 29, No. 5, pp. 381-385.

YouTube video entitled: "How to Round Corners in Illustrator," uploaded Sep. 6, 2017 by user "Mohamed Achraf" [retrieved on Jul. 7, 2022]. Retrieved from the Internet: <URL:https://www.youtube.com/watch?v=q8Cyd0sqY6A>, 3 pages.

Andersson, K. E. et al., "CNS Involvement in Overactive Bladder—Pathophysiology and Opportunities for Pharmacological Intervention", Drugs, (2003), vol. 63, No. 23, pp. 2595-2611.

Anonymous, "Re: Round corners (fillet) in Illustrator CS6", in: Stack Exchange [online], Graphic Design, Jan. 22, 2018; 17:52 [retrieved on Feb. 6, 2024]. Retrieved from the Internet: <URL:https://graphicdesign.stackexchange.com/questions/104349/round-corners-fillet-in-illustrator-cs6>, 10 pages.

Anonymous, Lumbar Decompression Surgery: When it's used, Datasheet [online], National Health Service, 2022. Retrieved from the Internet: <URL:https://www.nhs.uk/conditions/lumbar-decompression-surgery/why-its-done/#:-:text=Cauda%equina%20syndrome%20a.is%20severe%20or%20getting%20worse, 2 pages.

Anonymous, Vital Signs, Datasheet [online], Cleveland Clinic [retrieved on Nov. 22, 2021]. Retrieved from the Internet: <URL:https://my.clevelandclinic.org/health/articles/10881-vital-signs, 19 pages.

Bruckenstein, S. et al., "An experimental study of nonuniform current distribution at rotating disk electrodes", Journal of the Electrochemical Society, (1970), vol. 117, No. 8, pp. 1044-1048.

(56)  References Cited

OTHER PUBLICATIONS

Communication Pursuant to Article 94(3) EPC in counterpart European Patent Application No. 12760696.0 mailed Nov. 9, 2017, 5 pages.
Communication Pursuant to Article 94(3) EPC in counterpart European Patent Application No. 12847885.6 mailed Apr. 15, 2016, 5 pages.
Communication Pursuant to Article 94(3) EPC in counterpart European Patent Application No. 12847885.6 mailed Feb. 16, 2017, 5 pages.
Communication Pursuant to Article 94(3) EPC in counterpart European Patent Application No. 12848368.2 mailed May 9, 2018, 5 pages.
Communication Pursuant to Article 94(3) EPC in counterpart European Patent Application No. 14765477.6 mailed Nov. 14, 2018, 5 pages.
Communication Pursuant to Article 94(3) EPC in counterpart European Patent Application No. 14765477.6 mailed Sep. 27, 2019, 6 pages.
Communication Pursuant to Article 94(3) EPC in counterpart European Patent Application No. 14849355.4 mailed Jul. 20, 2018, 6 pages.
Communication Pursuant to Article 94(3) EPC in counterpart European Patent Application No. 15834593.4 mailed Jul. 17, 2019, 4 pages.
Communication Pursuant to Article 94(3) EPC in counterpart European Patent Application No. 15834593.4 mailed Jul. 30, 2020, 5 pages.
Communication Pursuant to Article 94(3) EPC in counterpart European Patent Application No. 17826212.7 mailed Dec. 21, 2020, 7 pages.
Communication Pursuant to Article 94(3) EPC in counterpart European Patent Application No. 18807366.2 mailed Mar. 22, 2023, 4 pages.
Communication Pursuant to Article 94(3) EPC in counterpart European Patent Application No. 21166801.7 mailed Mar. 7, 2024, 6 pages.
Communication Pursuant to Article 94(3) EPC in counterpart European Patent Application No. 24153829.7 mailed Apr. 4, 2025, 5 pages.
Communication Pursuant to Rule 114(2) EPC in counterpart European Patent Application No. 12847885.6 mailed Mar. 27, 2015, 28 pages.
Coursera, "What is Machine Learning? Definition, Types, and Examples," Coursera, May 20, 2025. Retrieved from the Internet: <URL:https://www.coursera.org/articles/what-is-machine-learning>, 12 pages.
Courtine, G. et al., "Modulation of multisegmental monosynaptic responses in a variety of leg muscles during walking and running in humans", Journal of Physiology, (2007), vol. 582, No. 3, pp. 1125-1139.
Danner, S. M. et al., "Can the Human Lumbar Posterior cols. be Stimulated by Transcutaneous Spinal Cord Stimulation? A modeling study", Europe PMC funders author manuscripts, Artificial Organs, (2011), vol. 35, No. 3, pp. 257-262.
Decision to Refuse a European Patent Application in counterpart European Patent Application No. 15834593.4 mailed Oct. 28, 2021, 24 pages.
Desantana, J. M. et al., "Effectiveness of Transcutaneous Electrical Nerve Stimulation for Treatment of Hyperalgesia and Pain", Current Rheumatology Reports, (2008), vol. 10, pp. 492-499.
Drummond, G. B. et al., "Thoracic impedance used for measuring chest wall movement in postoperative patients", British Journal of Anaesthesia, (1996), vol. 77, No. 3, pp. 327-332.
Dubinsky, R. M. et al., ""Assessment: Efficacy of transcutaneous electric nerve stimulation in the treatment of pain in neurologic disorders (an evidenced-based review)"", Report of the Therapeutics and Technology Assessment Subcommittee of the American Academy of Neurology, Neurology, (2010), vol. 74, No. 2, pp. 173-176.

Edgerton, V. R. et al., "Epidural stimulation of the spinal cord in spinal cord injury: current status and future challenges", Expert Review of Neurotherapeutics, (2011), vol. 11, No. 10, pp. 1351-1353.
EPO Communication and Supplementary European Search Report in counterpart European Patent Application No. 17745012.9 mailed Aug. 13, 2019, 8 pages.
European Opposition filed in counterpart European Patent Application No. 17826212.7 mailed Dec. 2, 2022, 56 pages.
European Reply to Communication in counterpart European Patent Application No. 12847885.6 mailed Oct. 24, 2016, 4 pages.
Extended European Search Report in counterpart European Patent Application No. 14765477.6 mailed Nov. 8, 2016, 10 pages.
Extended European Search Report in counterpart European Patent Application No. 14849355.4 mailed May 10, 2017, 7 pages.
Extended European Search Report in counterpart European Patent Application No. 15834593.4 mailed Apr. 4, 2018, 7 pages.
Extended European Search Report in counterpart European Patent Application No. 15836927.2 mailed Mar. 1, 2018, 9 pages.
Extended European Search Report in counterpart European Patent Application No. 16825005.8 mailed Feb. 19, 2019, 8 pages.
Extended European Search Report in counterpart European Patent Application No. 16833973.7 mailed Dec. 13, 2018, 6 pages.
Extended European Search Report in counterpart European Patent Application No. 18744685.1 mailed Sep. 7, 2020, 8 pages.
Extended European Search Report in counterpart European Patent Application No. 19201998.2 mailed Apr. 21, 2020, 7 pages.
Extended European Search Report in counterpart European Patent Application No. 19851613.0 mailed Apr. 19, 2022, 9 pages.
Extended European Search Report in counterpart European Patent Application No. 19852797.0 mailed Apr. 19, 2022, 6 pages.
Extended European Search Report in counterpart European Patent Application No. 20163794.9 mailed Sep. 18, 2020, 7 pages.
Extended European Search Report in counterpart European Patent Application No. 20164082.8 mailed Jul. 21, 2020, 7 pages.
Extended European Search Report in counterpart European Patent Application No. 20175385.2 mailed Jan. 22, 2021, 8 pages.
Extended European Search Report in counterpart European Patent Application No. 21166801.7 mailed Aug. 17, 2021, 11 pages.
Extended European Search Report in counterpart European Patent Application No. EP12847885.6 mailed May 6, 2015, 7 pages.
Extended European Search Report in counterpart European Patent Application No. 19211698.6 mailed May 28, 2020, 6 pages.
Fong, A J. et al., "Recovery of control of posture and locomotion after a spinal cord injury: solutions staring us in the face", Progress in Brain Research, Elsevier Amsterdam, Netherlands, (2009), vol. 175, Chapter 25, pp. 393-418.
Gerasimenko, Y. et al., "Initiation and modulation of locomotor circuitry output with multisite transcutaneous electrical stimulation of the spinal cord in noninjured humans", Journal of Neurophysiology, (2015), vol. 113, No. 3, pp. 834-842.
Gerasimenko, Y. et al., "Novel and Direct Access to the Human Locomotor Spinal Circuitry", Journal of Neuroscience, (2010), vol. 30, No. 10, pp. 3700-3708.
Gerasimenko, Y. et al., "Transcutaneous electrical spinal-cord stimulation in humans", Annals of Physical and Rehabilitation Medicine, (2015), vol. 58, No. 4, pp. 225-231.
"Aching knee or sore back? New app helps doctors treat pain," medicalxpress.com, (2017), Retrieved from the Internet: < URL: https://medicalxpress.com/news/2017-05-aching-knee-sore-app-doctors. html>, 1 page.
"Back pain and body posture infographic," Alamy.com, (2017), Retrieved from the Internet: <URL:https://www.alamy.com/stock-photo-back-pain-and-body-posture-infographic-with-anatomical-illustrations-141494074.html?imageid=27CC5905-F123-4DSC-847A4C76D50631C1&p=313080&pn=1&search Id=526c9d4db7f91a3e259d7b785fa370c3&searchtype=0>, 2 pages.
European Patent Office Action in counterpart European Patent Application No. 25165562.7 mailed Sep. 2, 2025, 9 pages.
Ichiyama et al., "Step training reinforces specific spinal locomotor circuitry in adult spinal rats," Journal of Neuroscience, (2008), vol. 28, No. 29, pp. 7370-7375.

(56) References Cited

OTHER PUBLICATIONS

"Male and female muscle and skeletal systems," Shutterstock.com, (2021), Retrieved from the Internet: <URL: https://www.shutterstock.com/image-illustration/male-female-muscle-skeletal-systems-xray-1895443960>, 2 pages.

"Screenshots of the electric patient-reported outcome app final prototype," Researchgate.net, (2020), Retrieved from the Internet: <URL:https://www.researchgate.net/figure/Screenshots-of-the-electronic-patient-reported-outcome-app-final-prototype_fig>, 1 page.

* cited by examiner

Figure 4:
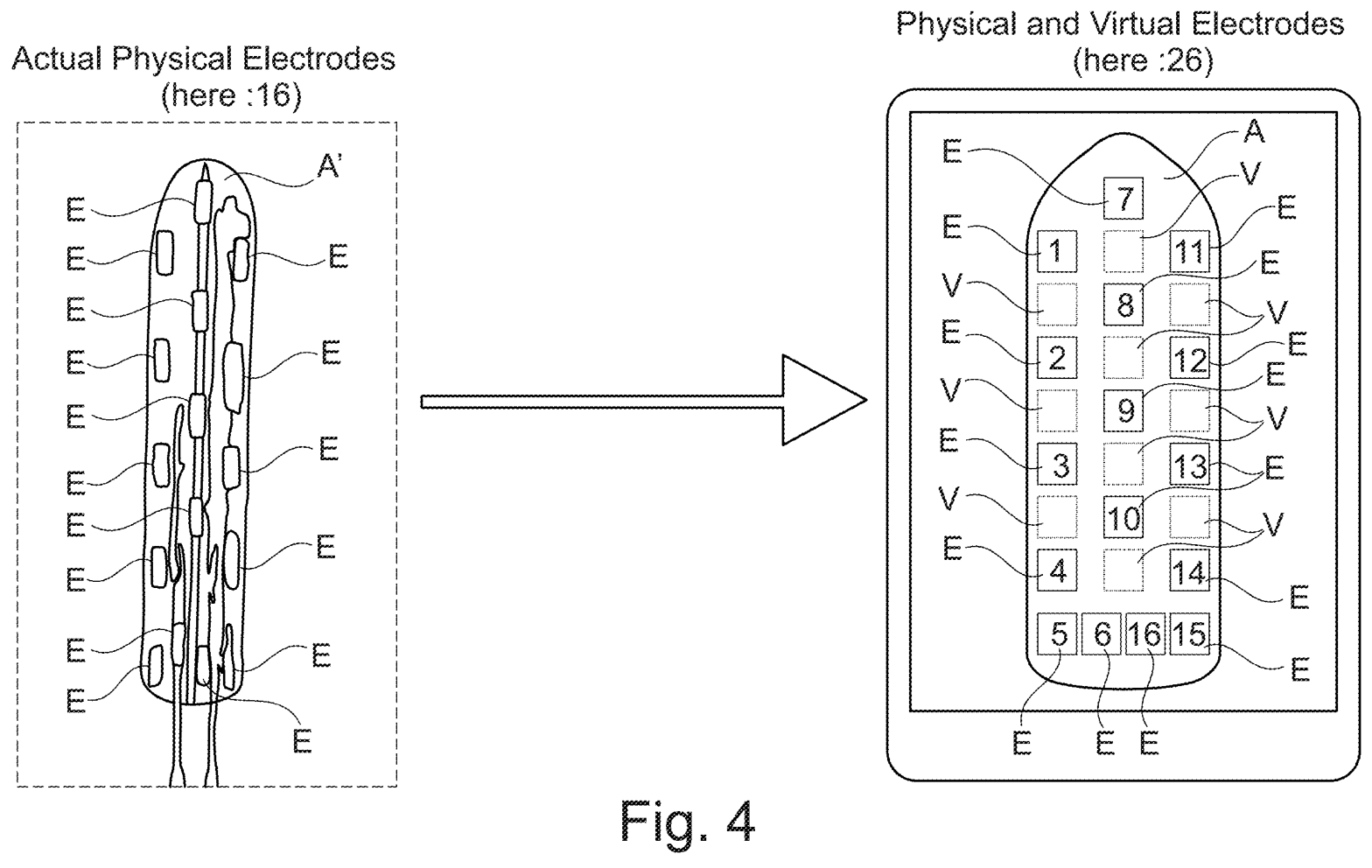

Physical and Virtual Electrodes
(here :26)

A
V E
E E
E V
V E
E E
E V
E
E E
E
E E E
E E E 7   11
8   12
9   13
10  14
    15
16
6
5

Actual Physical Electrodes
(here :16)

Current : 1.5 mA

Frequency : 1.0000Hz
Pulse-width : 0.3ms

PLANNING AND/OR CONTROL SYSTEM FOR A NEUROMODULATION SYSTEM

CROSS REFERENCE TO RELATED APPLICATION

The present application claims priority to European Patent Application No. EP 19209911.7 filed on Nov. 19, 2019. The entire contents of the above-listed application is hereby incorporated by reference for all purposes.

TECHNICAL FIELD

Disclosed embodiments relate to control systems for tissue stimulating systems, in some embodiments a planning and/or control system for a system for providing neuromodulation, especially neurostimulation for a patient.

BACKGROUND AND SUMMARY

The disclosed embodiments further relate to a method for planning neuromodulation, and in some embodiments neurostimulation for a patient.

The spinal cord is an integral part of the central nervous system (CNS). Spinal cord injury (SCI), but also other disorders (e.g. stroke, multiple sclerosis, autonomic failure, autonomic neuropathy or cancer of the neurological tissue which impair operation of descending sympathetic pathways that normally facilitate control of autonomic functions) result in motor deficits. For instance, SCI interrupts the communication between the spinal cord and supraspinal centers, depriving these sensorimotor circuits from the excitatory and modulatory drives necessary to produce movement. However, SCI also results in sensory deficits and in autonomic dysfunctions. In particular, SCI results in disconnection of some, most, or all descending sympathetic pathways that carry signals responsible for regulating arterial blood pressure, heart rate and/or gut and/or bladder function.

Spinal cord stimulation (SCS) is a well-established neuromodulatory therapy not only for restoring locomotion/motoric function after spinal cord injury or central nervous diseases, but also for treating inter alia pain and/or restoring autonomic function.

Neuromodulation, in particular neurostimulation, in particular SCS can be applied to a subject by a neuromodulation system comprising at least one electrode array comprising at least one electrode. Neuromodulation systems may further comprise at least one of a controller, e.g. a microcontroller, a processor, e.g. a microprocessor, a pulse generator, in some embodiments an implantable pulse generator, a sensor, a communication module, a telemetry module.

The electrode array, e.g. comprised in a lead paddle, can be applied for percutaneous electrical stimulation, transcutaneous electrical nerve stimulation (TENS), epidural electrical stimulation (EES), subdural electrical stimulation (SES), functional electrical stimulation (FES) and/or all neurostimulation and/or muscle stimulation applications that use at least one electrode array and/or at least one electrode.

Lead paddles are for example described in U.S. Pat. No. 8,108,051B2, US 2013/0096662 A1, US 2012/0006793A1 and EP3013411A1.

A neuromodulation system, especially a neurostimulation system for a patient suffering from motoric dysfunction and/or autonomic dysfunction may require programming to define which stimulation settings can be used to evoke certain muscles or muscle groups. Such muscles and/or muscle groups may be responsible for locomotion of the arms or legs, and/or responsible for e.g. bowel movement, sphincter control, bladder control and/or sexual function. Such programming of stimulation parameters may be performed by a user, such as a clinical professional, a physiotherapist and/or the patient himself, and facilitated by a computer-driven application. Neurostimulation, in particular multi-channel and/or variable neurostimulation may require an interface to create the stimulation program and a stimulation system to deliver the stimulation. A user may select specific electrodes via a user interface on which he would like to perform stimulation for a patient who's implanted with the lead comprising the electrode array.

EP3527258A1 discloses a system for an electrical neurostimulator coupled to a plurality of electrodes, comprising: a user-controlled input device configured for generating directional control signals; and control circuitry configured for sequentially defining a plurality of different ideal bipole/tripole configurations relative to the plurality of electrodes in response to the directional control signals, generating a plurality of stimulation parameter sets respectively corresponding to the plurality of ideal bipole/tripole configurations, each stimulation parameter set defining relative amplitude values for the plurality of electrodes that emulate the respective ideal bipole/tripole configuration, and instructing the neurostimulator to convey electrical energy to the plurality of electrodes in accordance with the plurality of stimulation parameter sets.

EP3285855B1 discloses a system for delivering neurostimulation including a programming control circuit and a user interface. The programming control circuit may be configured to generate stimulation parameters controlling delivery of neurostimulation pulses according to one or more stimulation waveforms associated with areas of stimulation each defined by a set of electrodes. The neurostimulation pulses are each delivered to an area of stimulation. The user interface may include a display screen and an interface control circuit. The interface control circuit may be configured to define the one or more stimulation waveforms and the areas of stimulation and may include a stimulation frequency module configured to display a stimulation rate table on the display screen. The stimulation rate table may present stimulation frequencies associated with each of the areas of stimulation for selection by a user.

Currently, leads comprising an electrode array comprising multiple electrodes with an intended use for neuromodulation offer a limited range of freedom since their resolution is confined by the number of electrodes. Options such as unipolar and multipolar stimulation increase field-steering capabilities, but the user is still limited by the fixed set of electrodes that he or she can pick from.

Therefore, the present disclosure provides a neuromodulation system which allows increasing neuromodulation options on a lead comprising an electrode array comprising electrodes.

This increasing of the neuromodulation options may be solved according to the disclosed embodiments by a planning and/or control system for a system for providing neuromodulation, including neurostimulation, at least comprising:

a graphical presentation module configured and arranged for providing graphical information about an electrode array comprising multiple electrodes and/or an implantation side for the electrode array comprising at least one target area, a selection module configured and arranged for determining a stimulation zone and/or a stimulation direction on the electrode array comprising at least one electrode and/or for individually selecting at least one electrode and/or for selecting at least one target area, a calculation module configured and arranged for determining a contribution of currents provided by electrodes of the stimulation zone and/or stimulation direction on the electrode array and/or the at least one electrode selected and/or to the at least one target area selected.

Consistent with the disclosed embodiments, the amount of stimulation options and/or stimulation resolution of a lead comprising an electrode array may be increased by using electrode and/or current weighting. Thus, the options for choosing stimulation options may no longer be constricted by selecting discrete electrodes (that means separate electrodes or one or more single electrode(s)) on a lead and/or electrode array but leverages the wide freedom of current weighting/balancing and presenting this in an intuitive way to a user using the system. Alternatively, and/or additionally, combining stimulation options with imaging may allow a user to create a root for stimulation or steering current to more naturally stimulate nerves rather than creating homogenous fields. The use of a graphical presentation module, a selection module and a calculation module combined into one strategy and made available for a system for providing neuromodulation, including neurostimulation may reduce limitations of stimulation options with current leads and/or electrode arrays and provide the patient the best possible stimulation.

In some embodiments, the system may use anatomical information about the dorsal root trajectory, to adapt the weighing of electrode currents, to steer the field, such (parallel to the trajectories) that maximum activation is obtained at target roots, while avoiding activation of the non-targeted roots.

The graphical presentation module may provide graphical information about an electrode array comprising physical electrodes and/or virtual electrodes. In some embodiments, physical electrodes may reflect physical electrodes of a corresponding neuromodulation system related to the system for planning and/or control system. In some embodiments, virtual electrodes may be represented by the graphical presentation module of the system only and may not reflect physical electrodes of a corresponding neuromodulation system related to the panning and/or control system according to the disclosed embodiments. In other words, virtual electrodes may be introduced by the system without physically introducing more physical electrodes. In some embodiments, any number of virtual electrodes may be introduced in addition to the physical electrodes. In some embodiments, virtual electrodes presented to a user may be more understandable and graspable than current-weighting or current-steering in percentages or absolute numbers. Overall, this enhances the options for choosing stimulation options.

In some embodiments, each virtual and/or physical electrode may be controlled independently. In some embodiments, this may enable that each virtual and/or physical electrode may be characterized by a different frequency and/or waveform.

In some embodiments, the user may be e.g. a therapist, a physiotherapist, a physician, a trainer, a medical professional, a patient and/or any person related to the patient.

In some embodiments, the target area may be or may comprise fictitious and/or realistic anatomical conditions of a mammal, in some embodiments a human being, such as the patient himself or a healthy individual. In some embodiments, the target area may be or may comprise at least one target nerve and/or nerve fiber and/or dorsal root and/or area of the spinal cord and/or tissue and/or area related to the spinal cord and/or muscle fiber and/or muscle.

In some embodiments, the target area could be augmented with an approximate neuronal model, e.g. neuronal fibers passing through dorsal roots. In some embodiments, the system may calculate contribution of currents based on neuronal simulations and/or anatomical conditions.

The selection module may be or may comprise a user interface. In some embodiments, the user interface may be a graphical user interface. In some embodiments, the selection module may be an input module. The selection module may comprise a mouse and/or a trackball and/or a joystick, a display and/or a touch screen and/or a touch pad and/or an acoustic signal and/or acoustic tone and/or a verbal command input. In some embodiments, the selection module may be configured and arranged for allowing a user to actuate at least one control element, including but not limited to axes, points, knots, buttons, arrows, hand signals, emojis, crosses and/or windows and/or text and/or shortcuts in order to modify graphical information.

In some embodiments, the selection module may enable to select information and/or links and/or strategies provided by the graphical presentation module.

In some embodiments, the stimulation zone may be or may comprise an area on a lead and/or electrode array comprising multiple electrodes, wherein the area comprises at least one electrode.

In some embodiments, a stimulation zone may also be or may comprise a stimulation vector and/or a stimulation direction and/or at least one single electrode.

The calculation module may be or may comprise at least one algorithm. In some embodiments, the calculation module may translate a selected stimulation zone and/or stimulation direction and/or the one or more electrodes individually selected and/or the at least one target area selected into a certain weighting, such as current weighting, on a real electrode array comprising electrodes, for stimulating a patient.

The calculation module may be configured and arranged for determining an equal contribution of currents provided by the electrodes of the stimulation zone and/or stimulation direction and/or the one or more electrodes individually selected and/or to the at least one target area selected. In some embodiments, a user may select a stimulation zone and/or a stimulation direction and/or one or more electrodes individually and current sourcing may be distributed equally over all electrodes and/or anodes selected. Alternatively, and/or additionally, a user may select at least one target area and current sourcing may be distributed equally over the electrodes located at the at least one target area. In some embodiments, this has the advantage that differences in excitation and/or excitability of different target nerves during equal stimulation may identified, which finally may enable optimizing stimulation protocols.

The calculation module may be configured and arranged for determining a weighted contribution of currents provided by the electrodes of the stimulation zone and/or stimulation direction and/or the at least one electrode individually selected and/or to the at least one target area selected. Overall, weighted contribution of currents, compared to homogenous fields, may enable more effective and closer to natural stimulation. In some embodiments, weighted contribution may direct a current to overcome neurological activity thresholds in an optimized matter. In some embodiments, the second spatial derivative, tangential to a neuron/nerve may be the driving force behind activation. A simple field normal to a fiber may not lead to predictive activation, yet a tangent directional field may lead to a predictive activation.

In some embodiments, for a stimulation direction, such as a stimulation vector, the weighting of electrodes may comprise distance and/or direction, in some embodiments with the origin of the stimulation direction as the reference.

The calculation module may be configured and arranged for determining the weighted contribution of currents provided by the electrodes of the stimulation zone and/or stimulation direction by calculating the Euclidean distance from an electrode to the stimulation zone and/or stimulation direction and/or to at least one point of the stimulation zone and/or stimulation direction.

In some embodiments, the Euclidean distance may be the ordinary distance between two points, here two electrodes and/or points of two electrodes. In some embodiments, it may be the straight-line distance between two points and/or two electrodes and/or two points of electrodes. In some embodiments, in a stimulation zone comprising more than two electrodes, this may have the advantage that the distance and the weighting of two electrodes is not affected by the addition of a third electrode to the analysis. Overall, weighting of each electrode of a stimulation zone and/or stimulation direction, based on the absolute and/or relative distance of the respective electrode of the stimulation zone and/or stimulation direction to one point of the stimulation zone and/or stimulation direction may be enabled. This may provide decreased stimulation intensity, the further an electrode of the stimulation zone is positioned away from a specific stimulation center of a stimulation zone. This may enable close to natural stimulation.

In some embodiments, the Euclidean distance may be the ordinary distance between two points, here e.g. two nerves and/or nerve fibers and/or parts of nerves and/or parts of nerve fibers of at least one target area. In some embodiments, it is the straight-line distance between e.g. two nerves and/or nerve fibers and/or parts of nerves and/or parts of nerve fibers of at least one target area. Overall, weighting of nerves and/or nerve fibers and/or parts of nerves and/or parts of nerve fibers of at least one target area, based on the absolute and/or relative distance of the respective nerve and/or nerve fiber and/or part of a nerve and/or part of a nerve fiber of the target area to one point of the target area may be enabled. This may enable that e.g. decreased stimulation intensity is provided, the further a nerve and/or nerve fiber and/or part of nerve and/or part of nerve fiber of at least one target area is from a specific stimulation center of a target area. This may enable close to natural stimulation.

The calculation module may be configured and arranged for determining the weighted contribution of currents provided by the electrodes of the stimulation zone and/or the stimulation direction and/or at least one electrode individually selected based on a generated field of neighbor electrodes. In some embodiments, this may enable soft transitions of the current strengths of adjacent electrodes. Overall, this may enable close to natural stimulation.

The calculation module may be configured and arranged for determining the weighted contribution of currents provided by the electrodes of the stimulation zone and/or the stimulation direction and/or the at least one electrode individually selected and/or to the at least one target area selected by a numerical method. In some embodiments, this approach may use a personalized patient model comprising the targeted and unwanted nerve locations (crosstalk), and which has computed for N electrode configurations the 3D potential distributions, as well as the activation potentials and/or selectivity indices. In some embodiments, based on the stimulation zone and/or the stimulation direction and/or the at least one electrode individually selected and/or the at least one target area selected the numerical method may optimize the weighting of electrode intensities for maximizing a selectivity index, or for maximizing the target while minimizing sensitive areas. Overall, this may enable stimulation adapted to patient specific needs, i.e. patient specific stimulation.

In some embodiments, different frequencies and/or pulse widths may be applied to different electrodes to create a stimulation zone. In some embodiments, a user may select a certain zone and intends the zone to have 130 Hz stimulation, which may then be achieved by delivering differing stimulation frequencies to its surrounding electrodes, and the frequency of 130 Hz in the stimulation zone may be achieved by amplification (overlapping, or constructive interference) or cancellation interference.

Further, the system may determine for which intended muscles/roots, a certain waveform should be used, e.g. a low frequency, a higher frequency, or a burst (e.g. triplets/quadruplets, with different burst frequency) waveform. In this case, the system may use knowledge of neurophysiology, i.e. which muscles (agonists/antagonists) and/or roots to determine if a higher frequency, or a burst frequency is required to increase activation of target muscles and/or roots, while keeping unwanted muscles and/or roots less exposed.

The calculation module may be configured and arranged to feature an algorithm to determine the weighted contribution of currents to the benefit of power efficiency. This algorithm may be appended to any of the previously mentioned calculation module implementations. This algorithm may interpret the input weighted electrode configuration and optimize it such that a new configuration is created that creates a considerably similar electrical field with the same effect on the effectuated neural tissue, yet with better power efficiency. In some embodiments, with the increased stimulation freedom offered to the system by the 'Virtual Electrodes' concept, the search-space for more power-efficient settings to the algorithm is also increased. In addition to the algorithm altering the current weighting, the algorithm may further achieve power-efficiency effects by combining this with reduction or increase of the amount of allocated electrodes (to reduce impedance), or may update the required stimulation current or total charge required to achieve the neurostimulation.

The system may further comprise at least one computer-assisted module configured and arranged for at least partially automatically determining a stimulation zone and/or a stimulation direction on the electrode array comprising at least one electrode and/or for at least partially automatically selecting at least one electrode, optionally based on medical imaging superimposing. In some embodiments, medical images may be obtained by MRI, CT, X-Ray, photography, etc. Alternatively, and/or additionally, anatomical models could be used. In some embodiments, this may enable finding optimal zones and/or targets for stimulation, specifically adapted to the patient's anatomy and needs.

In other words, the stimulation direction and/or stimulation zone on an electrode array comprising at least one electrode may be either selected manually by a user or automatically or semi-automatically by identifying a target area from anatomical data.

Accordingly, embodiments of the present disclosure provide: On the visualization of the electrode overlapped on the anatomical model (with roots visible), the desired stimulation zone may be drawn (and direction) in order to target the roots of interest.

Furthermore, this zone may be determined automatically when a software identifies the roots automatically from the anatomical model (e.g. MRI).

The system may further comprise at least one of a display, a controller, a programmer, a communication module, a telemetry module, a stimulation device, an electrode, a sensor and/or a sensor network.

In some embodiments, the system may be a closed-loop system or an open-loop system.

In some embodiments, the system allows both closed-loop or open loop functionality. In this regard, the user may switch between these options or there may be routines or control elements that can do or propose such a switch from closed-loop to open-loop and vice versa.

In some embodiments, the system may be related to a system for providing neuromodulation, in some embodiments neurostimulation to a patient. The system for providing neuromodulation, in some embodiments neurostimulation to a patient may comprise at least one of a controller, a programmer, a communication module, a telemetry module, a stimulation device comprising an electrode array comprising multiple electrodes, a sensor and/or a sensor network.

According to the disclosed embodiments a method is disclosed, the method being performed with the system described above.

In some embodiments, a method for planning neuromodulation, especially neurostimulation, may comprise at least the steps of:

providing graphical information about an electrode array comprising multiple electrodes and/or an implantation side for the electrode array comprising at least one target area, determining a stimulation zone and/or a stimulation direction on the electrode array comprising at least one electrode and/or individually selecting at least one electrode and/or selecting at least one target area, determining a contribution of currents provided by electrodes of the stimulation zone on the electrode array and/or the at least one electrode selected and/or to the at least one selected target area.

In some embodiments, the graphical information about the electrode array may comprise actual physical electrodes and/or virtual electrodes.

The method may further comprise the step of determining an equal contribution of currents provided by the electrodes of the stimulation zone and/or the stimulation direction and/or at least one electrode individually selected and/or to the at least one target area selected.

In some embodiments, the method may further comprise the step of determining a weighted contribution of currents provided by the electrodes of the stimulation zone and/or the stimulation direction and/or at least one electrode individually selected and/or to the at least one target area selected.

The method may further comprise the step of determining the weighted contribution of currents provided by the electrodes of the stimulation zone and/or the stimulation direction by calculating the Euclidean distance from an electrode to the stimulation zone and/or the stimulation direction and/or to at least one point of the stimulation zone and/or stimulation direction.

The method may further comprise the step of determining the weighted contribution of currents provided by the electrodes of the stimulation zone and/or the stimulation direction and/or the at least one electrode individually selected based on a generated field of neighbor electrodes.

The method may further comprise the step of determining the weighted contribution of currents provided by the electrodes of the stimulation zone and/or the stimulation direction and/or at least one electrode individually selected and/or to the at least one target area selected by a numerical method.

The method may further comprise the step of least partially automatically determining a stimulation zone and/or a stimulation direction on the electrode array comprising at least one electrode and/or for at least partially automatically selecting at least one electrode, optionally based on medical imaging superimposing.

The method may further comprise the step of featuring an algorithm to determine the weighted contribution of currents to the benefit of power efficiency.

It is to be understood that both the foregoing general description and the following detailed description are exemplary and explanatory only and are not restrictive of the disclosed embodiments or the scope of the inventions as claimed. The concepts in this application may be employed in other embodiments without departing from the scope of the inventions.

BRIEF DESCRIPTION OF THE FIGURES

Further details and advantages of the disclosed embodiments shall now be disclosed in connection with the drawings. The accompanying drawings, which are incorporated in and constitute a part of this specification, illustrate several embodiments consistent with the disclosure and together with the description, serve to explain the principles of the disclosure. In the drawings:

FIG. 4 shows an example of an embodiment of an electrode array, comprising virtual electrodes, according to the disclosed embodiments;

DETAILED DESCRIPTION

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Figure 1:
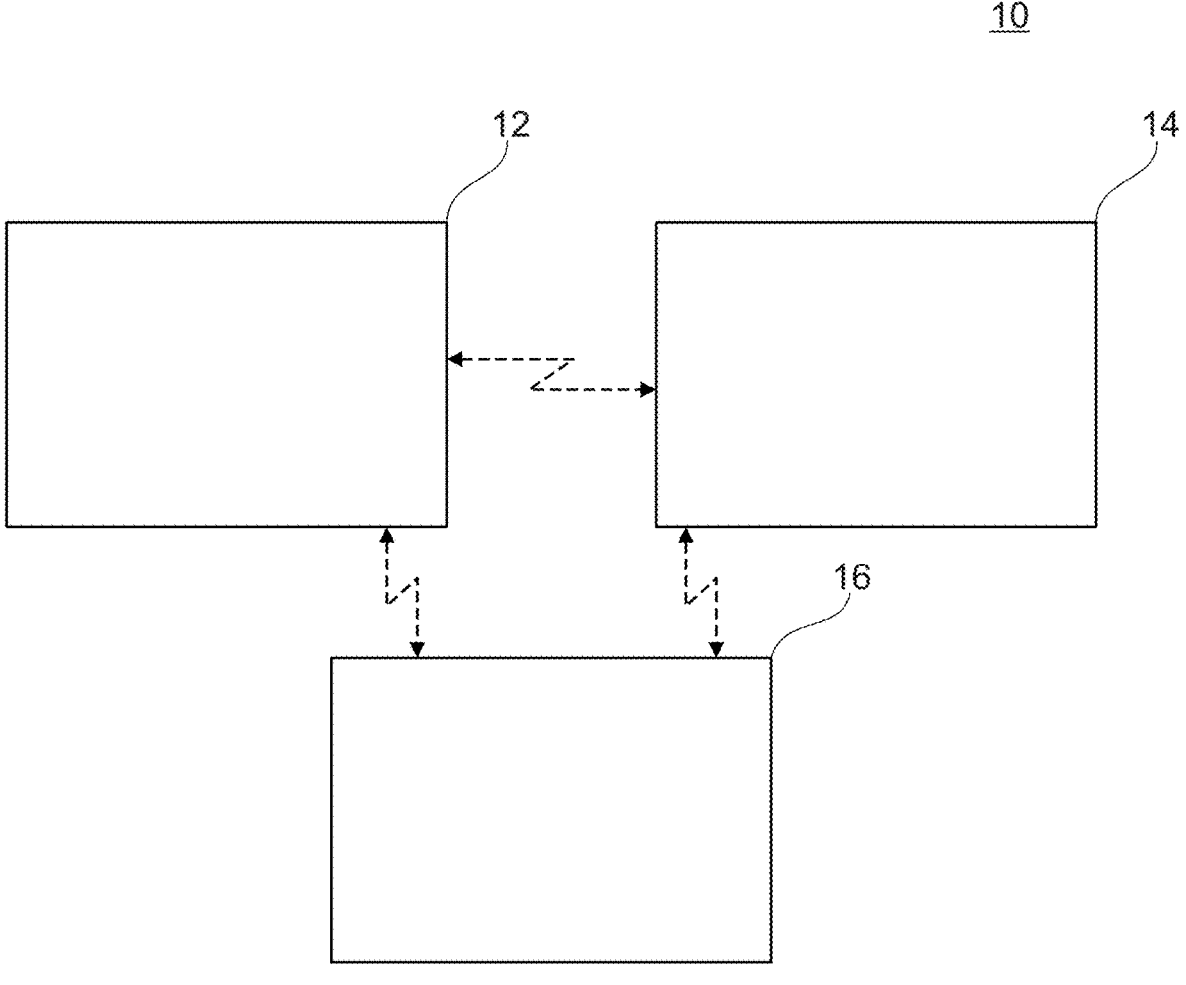
FIG. 1 shows a schematic overview of an embodiment of the planning and/or control system for a system for providing neuromodulation, especially neurostimulation according to the disclosed embodiments, with which the method according to the disclosed embodiments may be performed.

FIG. 1 shows a schematic overview of an embodiment of the planning and/or control system 10 for a system for providing neuromodulation, especially neurostimulation according to the disclosed embodiments, with which the method according to the disclosed embodiments may be performed.

The system 10 comprises a graphical presentation module 12, a selection module 14, and a calculation module 16. In some examples, the graphical presentation module 12, the selection module 14, and the calculation module 16 may be present on a single device, or one or more of the graphical presentation module 12, the selection module 14, and the calculation module 16 may be present on separate devices. The device(s) comprising the graphical presentation module 12, the selection module 14, and the calculation module 16 may include memory, one or more processors, and a communication subsystem, though other components and modules may also be included as known to those of skill in the art. In some aspects, the device(s) comprising the graphical presentation module 12, the selection module 14, and the calculation module 16 may be coupled to a user input device, a display, an electrode array comprising one or more electrodes, and/or other peripheral components.

Collectively, the various tangible components or a subset of the tangible components of the planning and/or control system 10 may be referred to herein as "logic" configured or adapted in a particular way, for example as logic configured or adapted with particular software, hardware, or firmware and adapted to execute computer readable instructions. The processors may be single core or multicore, and the programs executed thereon may be configured for parallel or distributed processing. The processors may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration, that is, one or more aspects may utilize ubiquitous, convenient, on-demand network access to a shared pool of configurable computing resources that can be rapidly provisioned and released with minimal management effort or service provider interaction. Clouds can be private, public, or a hybrid of private and public, and may include Infrastructure as a Service (IaaS), Platform as a Service (PaaS) and Software as a Service (SaaS). In some aspects, logic and memory may be integrated into one or more common devices, such as an application specific integrated circuit, field programmable gate array, or a system on a chip.

In some embodiments, one or more of the device(s) of the planning and/or control system 10 may be any computing or mobile device, for example, mobile devices, tablets, laptops, desktops, PDAs, and the like, as well as virtual reality devices or augmented reality devices. Thus, in some embodiments, the device(s) may include a display and thus a separate display or user input device may not be necessary. In other aspects, the device(s) may be coupled to a plurality of displays.

The memory generally comprises a random-access memory ("RAM") and permanent non-transitory mass storage device, such as a hard disk drive or solid-state drive. The memory may store an operating system as well as the various modules and components discussed herein. It may further include devices which are one or more of volatile, non-volatile, dynamic, static, read/write, read-only, random access, sequential access, location addressable, file addressable and content addressable.

The communication subsystem may be configured to communicatively couple the modules within a device as well as communicatively coupling a device with one or more other computing and/or peripheral devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like.

In some embodiments, the graphical presentation module 12 is configured and arranged for providing graphical information about an electrode array A comprising multiple electrodes E, V and/or an implantation side for the electrode array A comprising at least one target area X.

The system 10 further comprises the selection module 14. In some embodiments, the selection module 14 is configured and arranged for determining a stimulation zone Z and/or a stimulation direction D on the electrode array A comprising at least one electrode E, V and/or for individually selecting at least one electrode E, V and/or for selecting at least one target area X.

The system 10 further the calculation module 16. In some embodiments, the calculation module 16 is configured and arranged for determining a contribution of currents provided by electrodes E, V of the stimulation zone Z and/or stimulation direction D on the electrode array A and/or the at least one electrode E, V selected and/or a to the at least one target area X selected.

In some embodiments, the graphical presentation module 12, the selection module 14 and the calculation module 16 may be connected. In some embodiments, the graphical presentation module 12, the selection module 14 and the calculation module 16 may be connected via a bidirectional connection. In some embodiments, the graphical presentation module 12, the selection module 14 and the calculation module 16 may be connected via a wireless link. In various embodiments, a unidirectional and/or cable-bound connection between the graphical presentation module 12, the selection module 14 and/or the calculation module 16 may be used.

In some embodiments, the graphical presentation module 12 provides graphical information about an electrode array A comprising multiple electrodes E, V. In various embodiments, the graphical presentation module 12 may provide additionally and/or alternatively graphical information abound an implantation side for the electrode array A comprising at least one target area X. In some embodiments, the graphical information about the implantation site could be patient-specific data. In some embodiments, the graphical information about the implantation site could be patient-specific MRI data, X-Ray data, pictures obtained during surgery, etc.

In some embodiments, the selection module 14 can be configured to determines a stimulation zone Z. In some embodiments, the selection module 14 can be configured to determine a stimulation zone Z based on a user input. In some embodiments, the selection module 14 may comprise a user interface. In various embodiments, the selection module 14 could additionally and/or alternatively determine a stimulation direction D on the electrode array A comprising at least one electrode E, V and/or for selecting at least one target area X, based on user input.

In some embodiments (not depicted in FIG. 1), system 10 could further comprise at least one of a display, a controller, a programmer, a communication module, a telemetry module, a stimulation device, an electrode, a sensor and/or a sensor network, as described above. For example, each of the modules described herein could be included as part of or coupled to a controller, where the controller includes a non-transitory memory (e.g., the memory described above) storing instructions that are executable by a processor (e.g., the processor described above) to perform the functions described herein.

In some embodiments (not depicted in FIG. 1), graphical presentation module 12 could in general provide graphical information about an electrode array A comprising actual physical electrodes E and/or virtual electrodes V. Graphical presentation module 12 could be configured to enable selection of one or more virtual electrodes V for use in stimulation. In some embodiments, selection of a virtual electrode may be mathematically equivalent to selection of physical electrodes and the assignment of current steering parameters (e.g., current weights, steering percentages, or similar percentages or absolute numbers describing the distribution of current) to the selected physical electrodes. However, configuring stimulation through the selection of one or virtual electrodes V may be conceptually simpler and easier to understand.

In some embodiments (not depicted in FIG. 1), calculation module 16 could be configured and arranged to determine an equal contribution of currents provided by the electrodes E, V of the stimulation zone Z and/or the stimulation direction D and/or the one or more electrodes E, V individually selected and/or to the at least one selected target area X.

In some embodiments (not depicted in FIG. 1), calculation module 16 could be configured and arranged to determine a weighted contribution of currents provided by the electrodes E, V of the stimulation zone Z and/or stimulation direction D and/or the at least one electrode E, V individually selected and/or to the at least one selected target area X.

In some embodiments (not depicted in FIG. 1), calculation module 16 could be configured and arranged to determine the weighted contribution of currents provided by the electrodes E, V of the stimulation zone Z and/or stimulation direction D by calculating the Euclidean distance from an electrode E, V to the stimulation zone Z and/or stimulation direction D and/or to at least one point of the stimulation zone Z and/or stimulation direction D.

In some embodiments (not depicted in FIG. 1), calculation module 16 could be configured and arranged to determine the weighted contribution of currents provided by the electrodes E, V of the stimulation zone Z and/or the stimulation direction D and/or at least one electrode E, V individually selected based on a generated field of neighbor electrodes E, V.

In some embodiments (not depicted in FIG. 1), calculation module 16 could be configured and arranged to determine which neighboring electrodes E, V, given what weighted contribution of currents, can create a specified stimulation vector and/or a stimulation direction D. In some embodiments (not depicted in FIG. 1), calculation module 16 could be configured and arranged for determining the weighted contribution of currents provided by the electrodes E, V of the stimulation zone Z and/or the stimulation direction D and/or the at least one electrode E, V individually selected and/or to the at least one target area X selected by a numerical method. In some embodiments, the a numerical method could use a personalized patient model M, e.g. a MRI based patient model M, that includes both targeted and unwanted (cross-talk) nerve locations, and which has computed for N electrode E, V configurations the 3D potential distributions, as well as the activation potentials/selectivity indices.

In some embodiments (not depicted in FIG. 1), system 10 may further comprise at least one computer-assisted module configured and arranged for at least partially automatically determining a stimulation zone Z and/or a stimulation direction D on the electrode array A comprising at least one electrode E, V and/or for at least partially automatically selecting at least one electrode E, V, optionally based on medical imaging superimposing (e.g., as described below with regards to FIG. 6).

In some embodiments (not depicted in FIG. 1), calculation module 16 could be configured and arranged to consider power efficiency in determining a weighted contribution of currents.

Based on the electrodes E, V of the stimulation zone Z and/or the stimulation direction D and/or the at least one electrode E, V individually selected and/or the at least one target area X indicated by the user, the calculation module 16 may use a (pre-computed, or online calculated) neuronal activation model, to optimize the weighting of electrode E, V intensities for maximizing the selectivity index, or for maximizing the target while minimizing the sensitive areas.

In some embodiments, system 10 may perform a method for planning neuromodulation, including neurostimulation, at least comprising the steps of:

providing graphical information about an electrode array A comprising multiple electrodes E, V and/or an implantation side for the electrode array A comprising at least one target area X, determining a stimulation zone Z and/or a stimulation direction D on the electrode array A comprising at least one electrode E, V and/or individually selecting at least one electrode E, V and/or selecting at least one target area X, determining a contribution of currents provided by electrodes E, V of the stimulation zone Z and/or the stimulation direction D on the electrode array A and/or the at least one electrode E, V selected and/or to the at least one selected target area X.

In general, the graphical information about the electrode array A may comprise physical electrodes E and/or virtual electrodes V.

The method may further comprise the step of determining an equal contribution of currents provided by the electrodes E, V of the stimulation zone Z and/or the stimulation direction D and/or at least one electrode E, V individually selected and/or to the at least one target area X selected.

The method may further comprise the step of determining a weighted contribution of currents provided by the electrodes E, V of the stimulation zone Z and/or the stimulation direction D and/or at least one electrode E, V individually selected and/or to the at least one target area X selected.

The method may further comprise the step of determining the weighted contribution of currents provided by the electrodes E, V of the stimulation zone Z and/or the stimulation direction D by calculating the Euclidean distance from an electrode E, V to the stimulation zone Z and/or the stimulation direction D and/or to at least one point of the stimulation zone Z and/or stimulation direction D.

The method may further comprises the step of determining the weighted contribution of currents provided by the electrodes E, V of the stimulation zone Z and/or the stimulation direction D and/or the at least one electrode E, V individually selected based on a generated field of neighbor electrodes E, V.

The method may further comprise the step of determining the weighted contribution of currents provided by the electrodes E, V of the stimulation zone Z and/or the stimulation direction D and/or at least one electrode E, V individually selected and/or to the at least one target area X selected by a numerical method.

The method may further comprise the step of least partially automatically determining a stimulation zone Z and/or a stimulation direction D on the electrode array A comprising at least one electrode E, V and/or for at least partially automatically selecting at least one electrode E, V, optionally based on medical imaging superimposing.

The method may consider power efficiency in determining the weighted contribution of currents. In general, the weighting may be presented as absolute numbers (e.g. in V, mA, A) and/or expressed as percentage of total current applied by involved electrodes E, V.

Examples of how to determine a stimulation zone Z and/or stimulation direction D and/or select individual electrodes E, V and/or at least one target area X are disclosed in FIGS. 2, 3, 4, 5, 6, 7 and/or 8.

Figure 2:
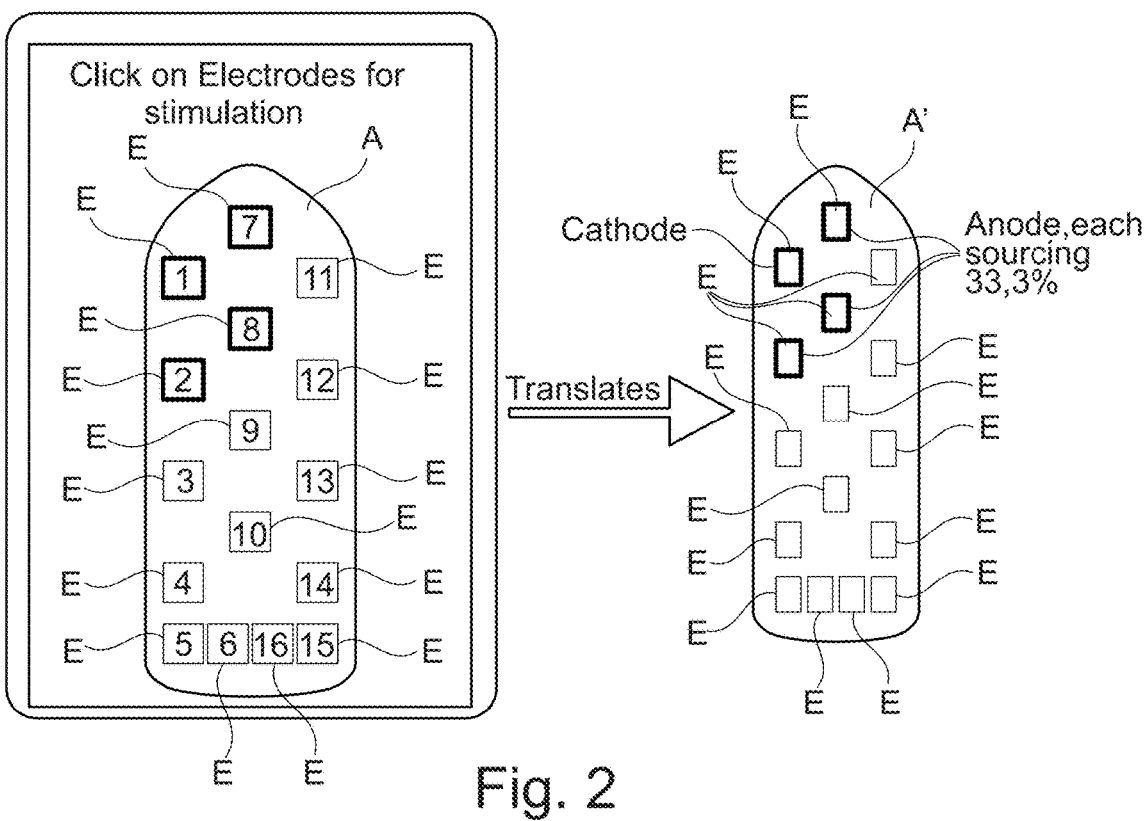
FIG. 2 shows an example of an equal contribution of currents provided by individually selected electrodes of an electrode array, according to the disclosed embodiments.

FIG. 2 shows an example of an equal contribution of currents provided by individually selected electrodes E, V of an electrode array A, determined by the calculation module 16 of the system 10 disclosed in FIG. 1. In this non-limiting example, the graphical information provided by graphical presentation module 12 of system 10 includes a depiction of an electrode array A comprising 16 electrodes E. System 10 can be connected to a neuromodulation system, the system including an electrode array A' and configured and arranged to provide neuromodulation to a patient. The electrode array A depicted in FIG. 2 can represent the electrode array A' of this connected neuromodulation system.

As depicted in FIG. 2, a tablet computer display that provides a graphical user interface (e.g., a touch screen) can be a selection module for system 10 (e.g., selection module 14). The disclosed embodiments are not so limited: any display and/or touch screen and/or programmer and/or mobile device can implement a selection module for system 10.

In some embodiments, the display can disclose the graphical information provided by the graphical presentation module 12. In some embodiments, a user can select electrodes E of the electrode array A' by touching corresponding electrodes E of the electrode array A displayed on the touch screen. Alternatively, the electrodes E could be selected via a mouse click. In general, the electrodes E may be selected by a mouse and/or a trackball and/or a joystick, a display and/or a touch screen and/or a touch pad and/or an acoustic signal and/or acoustic tone and/or a verbal command input. In general, the selection module 14 may allow a user to actuate at least one control element, including but not limited to axes, points, knots, buttons, arrows, hand signals, emojis, crosses and/or windows and/or text and/or shortcuts. In some embodiments, the user input is translated by the calculation module 16 into a certain weighting that may then be sent to the neuromodulation system.

In some embodiments, the neuromodulation provided by the neuromodulation system can be modified based on the user input. To continue the prior example, three electrodes (e.g., electrodes 7, 8, and 2) can be configured by the user using selection module 14 to serve as anodes. For example, they could have been individually selected through user interactions with the display. Calculation module 16 can allocate an equal amount of current to each of these anodes (e.g., 33.33% of the current sourced by electrode 1, the cathode in this example). In some embodiments, the related neuromodulation system could then provide stimulation to a patient using the electrode array A' and the determined current allocations.

Figure 3:
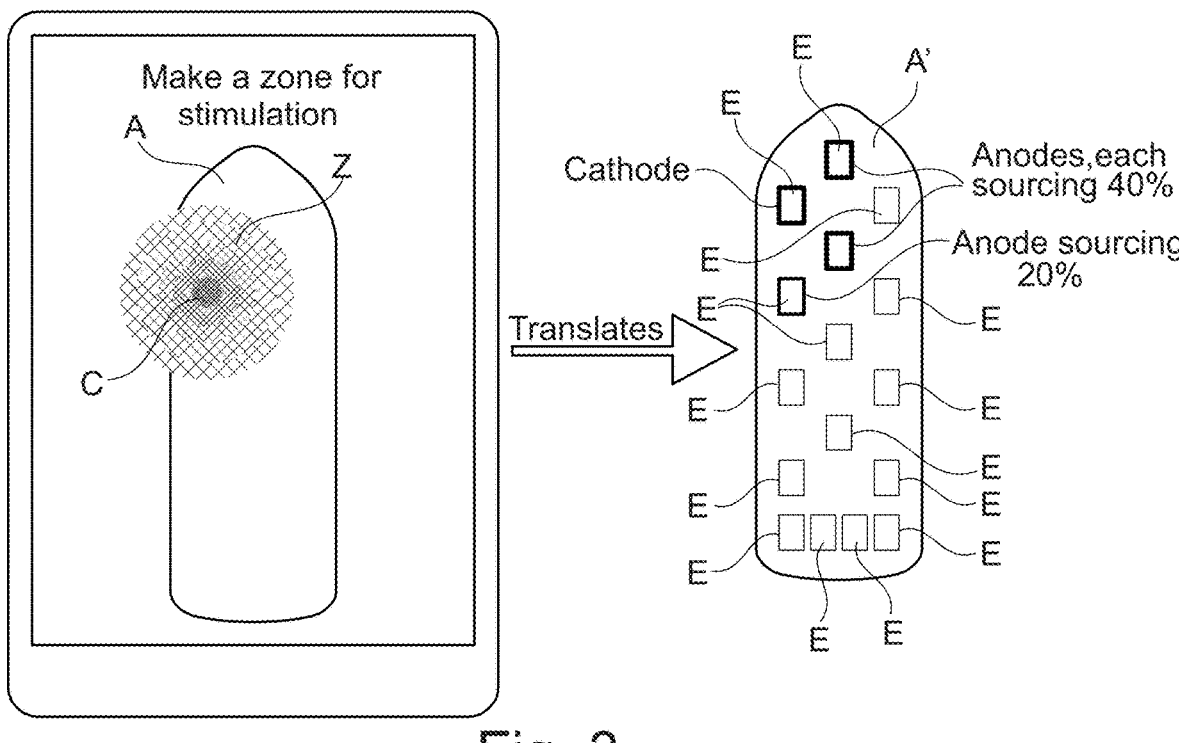
FIG. 3 shows an example of weighted contribution of currents provided by electrodes of a determined stimulation zone of an electrode array, according to the disclosed embodiments.

FIG. 3 shows an example of weighted contribution of currents provided by electrodes E of an electrode array A. In this nonlimiting example, the weighted contribution of currents establishes a stimulation zone Z. The weights of the contribution of currents can be determined by the calculation module 16. The stimulation zone Z can be determined through user interactions with graphical information provided by graphical presentation module 12. In this example, the graphical information can include a depiction of an electrode array A, which includes 16 electrodes E. The electrode array A can represent an electrode array A' of a neuromodulation system configured and arranged for providing neuromodulation to a patient.

As depicted in FIG. 3, a tablet computer display that provides a graphical user interface (e.g., a touch screen) can be a selection module for system 10 (e.g., selection module 14). In some embodiments, the display can implement a graphical presentation module (e.g., graphical presentation module 12). The disclosed embodiments are not so limited: any display and/or touch screen and/or programmer and/or mobile device can implement a selection module or graphical presentation module for system 10. Selection module 14 can be used to determine at least one stimulation zone Z (e.g., based on a user input).

In some embodiments, a user can select a stimulation zone Z by touching a corresponding location displayed on the touch screen. Alternatively, the stimulation zone could be determined via a mouse click. In general, the stimulation zone and/or a stimulation direction D may be determined through user interactions with a mouse and/or a trackball and/or a joystick, a display and/or a touch screen and/or a touch pad and/or an acoustic signal and/or acoustic tone and/or a verbal command input. In general, a user could interact with selection module 14 to actuate at least one control element, including but not limited to axes, points, knots, buttons, arrows, hand signals, emojis, crosses and/or windows and/or text and/or shortcuts. In some instances, the user input can cause a modification of existing stimulation parameters or existing neuromodulation.

Calculation module 16 can be configured to translate user input obtained using selection module 14 into stimulation parameters. In some instances, when system 10 is connected to a system for neuromodulation, the stimulation parameters may be sent to the neuromodulation system. The stimulation parameters can configure the neuromodulation system to provide neuromodulation according to the user input obtained using selection module 14. In some embodiments, the neuromodulation system can include an electrode array A'. The electrode array A' of the neuromodulation system could provide stimulation to a patient based on the determined stimulation parameters.

In some embodiments, calculation module 16 can translate the selected stimulation zone Z of an electrode array A into current weightings for physical electrodes E of the electrode array A'. In some embodiments, the weighted contribution of currents provided by the electrodes E may be determined by calculating the Euclidean distance from the electrodes E to the center C of the stimulation zone Z. In some embodiments, the weighted contribution of currents provided by the electrodes E can be determined by calculating the Euclidean distance from the electrodes E to any other point on the electrode array A, including the stimulation zone Z.

In some embodiments, calculation module 16 can determine current weightings for the electrodes of the electrode array A'. In the non-limited example provided in FIG. 3, the calculation module 16 determined a weighted contribution of currents provided by the electrodes E to implement the stimulation zone Z. This weighted contribution includes two anodes (each with 40% of the current) and one anode with 20% of the current (e.g., adding up to 100% of the current provided by the cathode). As would be appreciated by those of skill in the art, this example is not intended to be limiting.

FIG. 4 shows an example of an electrode array A that includes virtual electrodes V. In this nonlimiting example, the electrode array A can represent an electrode array A' of a neuromodulation system configured and arranged for providing neuromodulation to a patient. The electrode array A' can include a number of physical electrodes E (e.g., 16 physical electrodes in this example). The electrode array A can include 16 electrodes corresponding to the electrodes of electrode array A' and 10 virtual electrodes. In some embodiments, the virtual electrodes may not correspond to individual physical electrodes of A'. Instead, each virtual electrode may correspond to a weighted combination of currents provided by at least some of the physical electrodes E. Providing the weighted combination of currents through the at least some of the physical electrodes E may be equivalent to providing current through an electrode situated at the location of the virtual electrode. Electrode array A could alternatively include a different number of virtual electrodes.

As depicted in FIG. 4, a tablet computer can implement a selection module (e.g., selection module 14) and a graphical presentation module (e.g., graphical presentation module 12) for system 10. A display of the tablet computer can implement a graphical presentation module (e.g., graphical presentation module 12). The display can provide graphical information such as a graphical user interface. In this example, the display can depict electrode array A. In some embodiments, the display of the tablet computer can implement a selection module (e.g., selection module 14). As a non-limiting example, the display can be a touchscreen. The selection module can support user interactions that specify or select virtual electrodes V for electrode array A. The disclosed embodiments are not limited to implementation using a tablet computer: any display and/or touch screen and/or programmer and/or mobile device can implement a selection module or graphical presentation module for system 10.

In some embodiments, a user can specify or select virtual electrodes V for electrode array A by touching a corresponding icon or location displayed on the touch screen. Alternatively, the specification or selection of the virtual electrodes V can be determined via a mouse click. In general, the stimulation zone and/or a stimulation direction D may be determined through user interactions with a mouse and/or a trackball and/or a joystick, a display and/or a touch screen and/or a touch pad and/or an acoustic signal and/or acoustic tone and/or a verbal command input. In general, a user could interact with selection module 14 to actuate at least one control element, including but not limited to axes, points, knots, buttons, arrows, hand signals, emojis, crosses and/or windows and/or text and/or shortcuts. In some instances, the user input can cause a modification of existing stimulation parameters or existing neuromodulation.

In some embodiments, the user determines a stimulation zone Z on the electrode array A' by selecting a combination of physical electrodes E and virtual electrodes V on the electrode array A shown on the display. In some embodiments, the stimulation zone Z can be determined by selecting electrodes E, V via a mouse click. In general, the stimulation zone and/or a stimulation direction D may be determined by a mouse and/or a trackball and/or a joystick, a display and/or a touch screen and/or a touch pad and/or an acoustic signal and/or acoustic tone and/or a verbal command input.

In some embodiments, calculation module 16 can translate user input (e.g., selection of physical electrodes E and virtual electrodes V on an electrode array A, or the like) into simulation parameters (e.g., current weightings, or the like) that can be sent to the neuromodulation system. The neuromodulation system can provide stimulation according to the provided stimulation parameters using the physical electrodes E of electrode array A'. In this manner, a user can configure the stimulation using virtual electrodes, rather than current-weightings or current-steering in percentages. Configuration using virtual electrodes may be easier to comprehend and tune than configuration using current-weightings or current-steering in percentages.

In some embodiments, (not shown in FIG. 4), at least one key performance indicator, such as a selectivity index could be provided as graphical information provided by the graphical presentation module 12. The at least one key performance indicator can be provided before, during, or after selecting and/or interacting with electrodes E and virtual electrodes V of electrode array A. In some embodiments, the at least one key performance indicator can be provided dynamically (e.g., the value of the at least one key performance indicator can be repeatedly or continuously updated during such selection and/or interaction). In some embodiments, the value of the at least one key performance indicator can be determined based on at least one of an anatomical patient model or a neuronal activation model.

Figure 5:
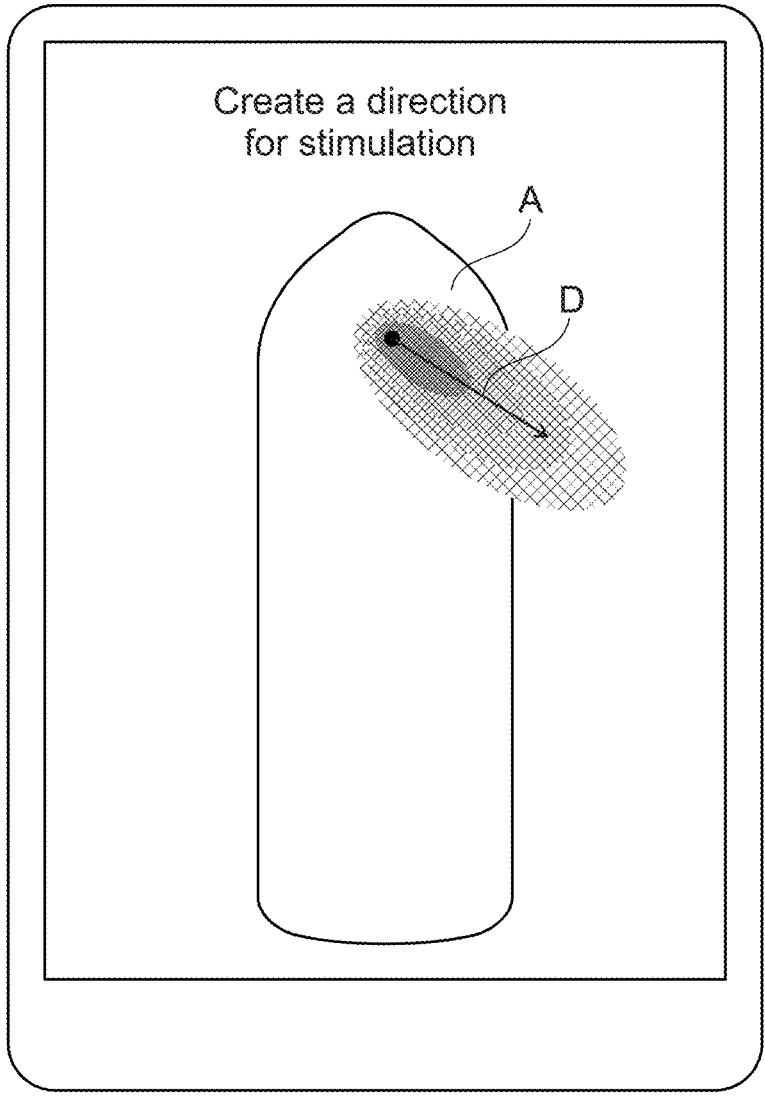
FIG. 5 shows an example of determining a stimulation direction, according to the disclosed embodiments.

FIG. 5 shows an example of determining a stimulation direction D, according to the disclosed embodiments. In this nonlimiting example, a user can interact with a touchscreen to specify the stimulation direction. For example, the user can touch a point on the touchscreen (e.g., using one or more digits, or the like) and drag to create a stimulation vector (e.g., an origin, direction, and extent of the stimulation). In some embodiments, the user can use multiple touches to add addition stimulation directions or modify or refine an existing stimulation direction (e.g., before, during, or after stimulation). The touchscreen can display an electrode array A that represents an electrode array A' of neuromodulation system configured and arrange to provide stimulation to a patient. A calculation module (e.g., calculation module 16) could be configured to determine stimulation parameters (e.g., selections of one or more electrodes E of electrode array A' to provide current, current contributions—weighted or equal—provided by such electrodes, or the like) that would result in a current flow in the specified stimulation direction D (e.g., having the specified origin, direction, or extent). The stimulation parameters can be provided to the neuromodulation system to provide the stimulation.

As depicted in FIG. 5, a tablet computer can implement a selection module (e.g., selection module 14) and a graphical presentation module (e.g., graphical presentation module 12) for system 10. A display of the tablet computer can implement a graphical presentation module (e.g., graphical presentation module 12). The display can provide graphical information such as a graphical user interface. In this example, the display can depict an electrode array A and the stimulation direction D. In some embodiments, the display of the tablet computer can implement a selection module (e.g., selection module 14). As a non-limiting example, the display can be a touchscreen. The selection module can support user interactions that specify or select the stimulation direction D. The disclosed embodiments are not limited to implementation using a tablet computer: any display and/or touch screen and/or programmer and/or mobile device can implement a selection module or graphical presentation module for system 10.

In some embodiments, at least one key performance indicator, such as a selectivity index could be provided as graphical information provided by the graphical presentation module 12. The at least one key performance indicator can be provided before, during, or after selecting and/or interacting with stimulation direction D. In some embodiments, the at least one key performance indicator can be provided dynamically (e.g., the value of the at least one key performance indicator can be repeatedly or continuously updated during such selection and/or interaction). In some embodiments, the value of the at least one key performance indicator can be determined based on at least one of an anatomical patient model or a neuronal activation model.

The disclosed embodiments are not limited to embodiments in which the user specifies a stimulation direction D by touching and dragging a digit, or the like. In some embodiments, the specification of the stimulation direction D can be determined via a mouse click. In general, the stimulation direction D may be determined through user interactions with a mouse and/or a trackball and/or a joystick, a display and/or a touch screen and/or a touch pad and/or an acoustic signal and/or acoustic tone and/or a verbal command input. In general, a user could interact with selection module 14 to actuate at least one control element, including but not limited to axes, points, knots, buttons, arrows, hand signals, emojis, crosses and/or windows and/or text and/or shortcuts. In some instances, the user input can cause a modification of existing stimulation parameters or existing neuromodulation.

Figure 6:
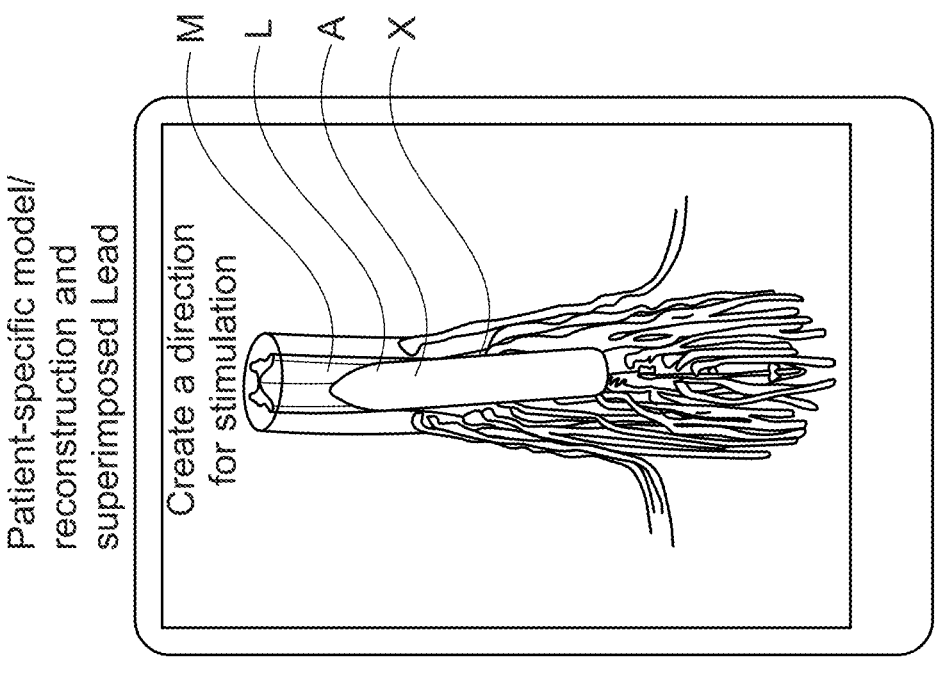
FIG. 6 shows two examples of graphical information provided by the graphical presentation module, combining an electrode array with a target area, according to the disclosed embodiments.

FIG. 6 shows two views of graphical information provided by the graphical presentation module (e.g., graphical presentation module 12), in accordance with disclosed embodiments. In this non-limiting example, each of the two views combine an electrode array A with a target area X, according to the disclosed embodiments. In the left view (titled "Patient-specific MRI and superimposed lead") a visualization of the target area X is displayed. The visualization can be based on patient-specific data obtained by Magnetic resonance imaging (MRI), X-Ray, computed tomography (CT) scan, pictures obtained during surgery, or other medical images. In the right view (titled "Patient-specific model/reconstruction and superimposed lead") a reconstruction or a model M of the target area X is displayed. In various embodiments, the target area X could be provided as a 2D model M and/or a 3D model M. In both views, as depicted in FIG. 6, the electrode array A can be superimposed on the visualization or reconstruction/model. In some embodiments, the electrode array A can be, or be part of a lead L. In such embodiments, as depicted in FIG. 6, the lead L can be superimposed on a target area X.

In some embodiments, a user could interact with a view to place or adjust a location of the electrode array A on at least one target area X by touching a location of electrode array A in the display with a digit and moving the electrode array A with the digit. In some 3D embodiments, the user could be able to control a position and orientation of the array A in three dimensions (e.g., by rotating the view, the array, or both). In various embodiments, a computer-assisted module may at least partially automatically determine a stimulation zone Z and/or a stimulation direction D on the electrode array A comprising at least one electrode E, V and/or for at least partially automatically selecting at least one electrode E, V optionally based on the medical imaging superimposing and/or a model M.

In some embodiments, at least one key performance indicator, such as a selectivity index could be provided as graphical information provided by the graphical presentation module 12. The at least one key performance indicator can be provided before, during, or after placement of the electrode array A on at least one target area X. In some embodiments, the at least one key performance indicator can be provided dynamically (e.g., the value of the at least one key performance indicator can be repeatedly or continuously updated during such placement). In some embodiments, the value of the at least one key performance indicator can be determined based on at least one of an anatomical patient model or a neuronal activation model.

As depicted in FIG. 6, a tablet computer can implement a selection module (e.g., selection module 14) and a graphical presentation module (e.g., graphical presentation module 12) for system 10. A display of the tablet computer can implement a graphical presentation module (e.g., graphical presentation module 12). The display can provide graphical information such as a graphical user interface. In this example, the display can depict a view of the electrode array A superimposed on the visualization or reconstruction/ model. In some embodiments, the display of the tablet computer can implement a selection module (e.g., selection module 14). As a non-limiting example, the display can be a touchscreen. The selection module can support user interactions that specify or select the position and/or orientation of at least one of the array or the reconstruction/model. The disclosed embodiments are not limited to implementation using a tablet computer: any display and/or touch screen and/or programmer and/or mobile device can implement a selection module or graphical presentation module for system 10.

The disclosed embodiments are not limited to embodiments in which the user places or adjusts a location of the electrode array A selecting and moving the electrode array A with a digit, or the like. In some embodiments, the placement of electrode array A can be determined via a mouse click. In general, the placement of electrode array A can be determined through user interactions with a mouse and/or a trackball and/or a joystick, a display and/or a touch screen and/or a touch pad and/or an acoustic signal and/or acoustic tone and/or a verbal command input. In general, a user could interact with selection module 14 to actuate at least one control element, including but not limited to axes, points, knots, buttons, arrows, hand signals, emojis, crosses and/or windows and/or text and/or shortcuts. In some instances, the user input can cause a modification of existing stimulation parameters or existing neuromodulation.

Figure 7:
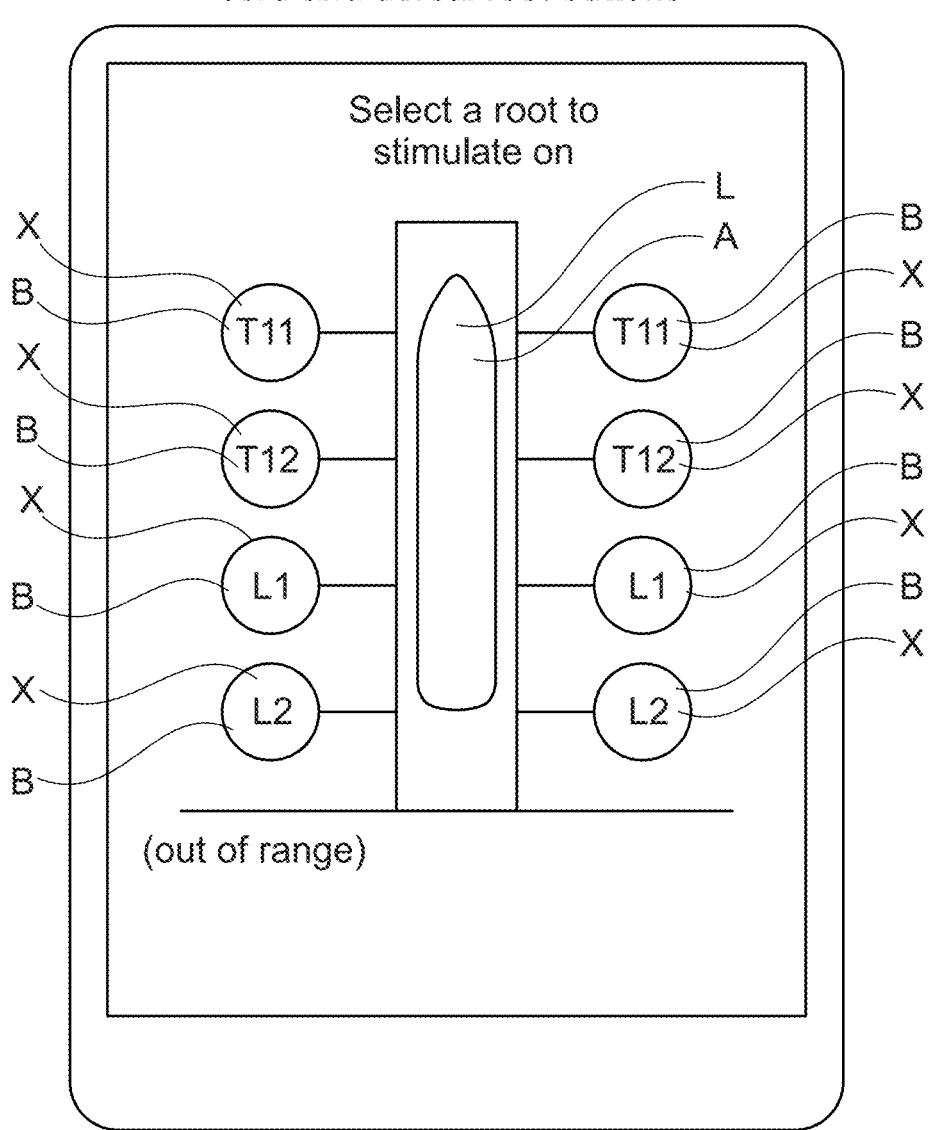
FIG. 7 shows a further example of graphical information provided by the graphical presentation module, combining an electrode array with at least one possible target area, according to the disclosed embodiments.

FIG. 7 shows a further example of graphical information provided by the graphical presentation module. In this example, the graphical information can include a schematic depiction. In some embodiments, the schematic depiction could include one or more elements, such as target area(s) X, the electrode array A, or the lead L (e.g., a lead L being or containing electrode array A). In some embodiments, the lead L or array A could be superimposed on one or more other elements. In general, schematic representations of muscles and/or organs could be positioned under an electrode array A and/or a lead L and/or or next to an electrode array A and/or a lead L.

Consistent with disclosed embodiments, icons or controls can represent the different elements depicted in the schematic representation. The icons or controls can be specific to the thing represented. The disclosed embodiments are not limited to any particular icons or representations. In some embodiments, the user can interact with the schematic representation to select an element for stimulation. Selecting the icon or control can cause calculation module 16 to translate the selection of the element into stimulation parameters (e.g., selections of one or more electrodes E of electrode array A' to provide current, current contributions—weighted or equal—provided by such electrodes, or the like) that would result in stimulation or activation of the selected element. The stimulation parameters can be provided to the neuromodulation system to provide the stimulation.

In various embodiments, the elements could include anatomical structures such as nerves, tissues, bones, muscles (e.g. leg/trunk muscles), glands, organs, or other anatomical structures. In some embodiments, the at least one target area X could be or include at least one of target nerve(s); nerve fiber(s); dorsal root(s); spinal cord area(s); tissue(s); organ(s); gland(s); or area(s) related to at least one of the spinal cord, muscle fiber, or muscles. In some embodiments, the schematic depiction could include one or more actions (e.g., movements; bladder, bowel, or sexual functions; or the like). In the same manner as selecting target area(s) X, action(s) could be selected. As described in greater detail below with regards to FIG. 8, stimulation can be applied according to the selected actions.

When selecting actions, the target area X could be alternatively and/or additionally be associated with kinematic model M, wherein intended muscles could be determined and weighted and/or unwanted crosstalk between agonists and antagonists could be assigned. In this manner, actions could be broken down into time-dependent, muscle-specific activation patterns. In this non-limiting example, such activation patterns could be translated into stimulation provided by electrodes E of the electrode array A'.

In some embodiments, the schematic depiction can be or include fictitious and/or realistic anatomical conditions of a mammal, in some embodiments a human being, such as the patient himself. In some embodiments, image data and/or 2D models M and/or 3D models M could be used as target area X for visual representation of anatomy of the patient, e.g. the dorsal roots.

As depicted in FIG. 7, for example, the schematic depicts the spinal cord as a rectangle and spinal nerves (e.g., pairs of thoracic nerves T11, T12 and lumbar nerves L1, L2) as buttons. The possible target areas X include the spinal cord and the spinal nerves. In this non-limiting example, the user can select at least one target area X, i.e. left and/or right thoracic nerve T11 and/or T12 and/or left and/or right lumbar nerve L1 and/or L2 by selecting the corresponding buttons B (e.g. by touching the corresponding button B with a digit).

In some embodiments, at least one key performance indicator, such as a selectivity index could be provided as graphical information provided by the graphical presentation module 12. The at least one key performance indicator can be provided before, during, or after selection and/or interaction with target area(s) X. In some embodiments, the at least one key performance indicator can be provided dynamically (e.g., the value of the at least one key performance indicator can be repeatedly or continuously updated during such selection and/or interaction). In some embodiments, the value of the at least one key performance indicator can be determined based on at least one of an anatomical patient model or a neuronal activation model.

As depicted in FIG. 7, a tablet computer can implement a selection module (e.g., selection module 14) and a graphical presentation module (e.g., graphical presentation module 12) for system 10. A display of the tablet computer can implement a graphical presentation module (e.g., graphical presentation module 12). The display can provide graphical information such as a graphical user interface. In this example, the display can depict a view of the schematic representation of the elements. In some embodiments, the display of the tablet computer can implement a selection module (e.g., selection module 14). As a non-limiting example, the display can be a touchscreen. The selection module can support user interactions that select or interact with the elements. The disclosed embodiments are not limited to implementation using a tablet computer: any display and/or touch screen and/or programmer and/or mobile device can implement a selection module or graphical presentation module for system 10.

The disclosed embodiments are not limited to embodiments in which the user selects or interacts with the schematic depiction using a touchscreen. In some embodiments, the selection or interaction can be determined via a mouse click. In general, the selection or interaction can be determined through user interactions with a mouse and/or a trackball and/or a joystick, a display and/or a touch screen and/or a touch pad and/or an acoustic signal and/or acoustic tone and/or a verbal command input. In general, a user could interact with selection module 14 to actuate at least one control element, including but not limited to axes, points, knots, buttons, arrows, hand signals, emojis, crosses and/or windows and/or text and/or shortcuts. In some instances, the user input can cause a modification of existing stimulation parameters or existing neuromodulation.

Figure 8:
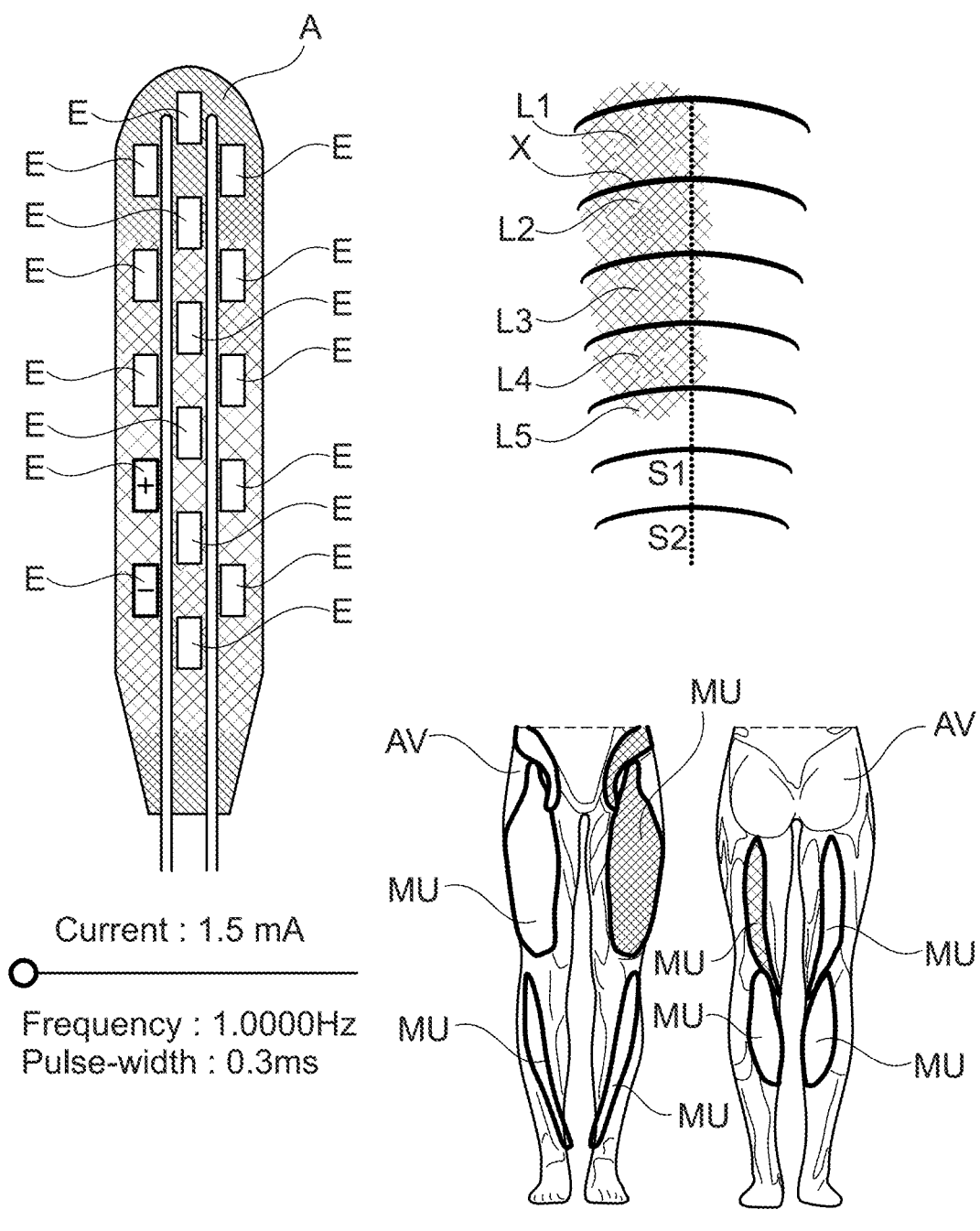
FIG. 8 shows a further example of graphical information provided by the graphical presentation module, according to the disclosed embodiments.

FIG. 8 shows a further example of graphical information provided by the graphical presentation module 12, according to the disclosed embodiments. In some embodiments, the graphical information provided by the graphical presentation module 12 includes possible target muscles MU to be stimulated, illustrated as different muscles MU of an avatar AV. In some embodiments, the graphical information provided by the graphical presentation module 12 further comprises a schema configured and arranged to illustrate a target area X based on target muscles MU. A user can select at least one target muscle MU by selecting at least one muscle MU, e.g. by touching the corresponding muscle MU of the avatar AV with a finger. As a non-limiting example, the user may select the right quadriceps Q. The selection module 14, based on the selected target muscle MU, can select a target area X. The target area X comprises spinal nerves L1-L5. In this non-limiting example, a patient is implanted with an electrode array A (electrode array A also shown in FIG. 8) capable of providing stimulation on the target area X. Calculation module 16 can determine a contribution of currents provided to the target area X selected in order to stimulate the muscle MU selected. In some embodiments, the contribution of currents provided to the target area X can gradually decreases from the center to the outside O of the target area X. The electrode array A provides stimulation to the target area X via selected electrodes E and selected stimulation parameters. In this non-limiting example, the current is 1.5 mA, the frequency is 1.0000 Hz and the pulse-width is 0.3 ms. However, other stimulation parameters could be generally possible.

As depicted in FIG. 8, a tablet computer can implement a selection module (e.g., selection module 14) and a graphical presentation module (e.g., graphical presentation module 12) for system 10. A display of the tablet computer can implement a graphical presentation module (e.g., graphical presentation module 12). The display can provide graphical information such as a graphical user interface. In this example, the display can depict muscles MU of an avatar AV. In some embodiments, the display of the tablet computer can implement a selection module (e.g., selection module 14). As a non-limiting example, the display can be a touch-screen. The selection module can support user interactions that select or interact with the elements. The disclosed embodiments are not limited to implementation using a tablet computer: any display and/or touch screen and/or programmer and/or mobile device can implement a selection module or graphical presentation module for system 10.

The methods of stimulation planning disclosed in FIGS. 2 to 8 can be combined or performed using a single system. For example, a user could select a target muscle (as in FIG. 8) or a target area (as in FIG. 7), or position the electrode (as in FIG. 6). The user could then cause the system to display the stimulation associated with that selection in terms of electrodes and weights (as in FIG. 2), stimulation zones (as in FIG. 3), virtual electrodes (as in FIG. 4), or stimulation directions (as in FIG. 5). The stimulation could then be refined or updated as described with regards to each of these figures. Such updating or refinement can be performed before, during, or after provision of the stimulation.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, are also regarded as included within the subject matter of the present disclosure.

What is claimed is:

1. A planning and/or control system for a system for providing neuromodulation, comprising:
   at least one processor;
   a non-transitory memory storing instructions that, when executed by the at least one processor, cause the at least one processor to perform steps comprising:
      providing graphical information about an electrode array overlapped on an anatomical imaging of a patient, the graphical information comprises at least one target area;

automatically recognizing dorsal root trajectory from the anatomical imaging; and determining, by receiving a selection of at least one of the at least one target area of the graphical information and translating the selection into a weighting of the electrode array based on the selection:
   a stimulation zone on the electrode array;
   non-targeted dorsal roots; and
   a contribution of currents provided by the electrode array, such that a stimulation field created by the electrode array avoid activation of the non-targeted roots;
wherein the electrode array comprises multiple electrodes, or an implantation side for the electrode array comprises at least one target area;
wherein each of the multiple electrodes is capable of independently delivering a different waveform.

2. The system of claim 1, wherein the graphical information about the electrode array comprises actual physical electrodes or virtual electrodes.

3. The system of claim 2, the steps further comprises determining an equal contribution of currents provided by the electrodes of the stimulation zone.

4. The system of claim 2, the steps further comprises determining a weighted contribution of currents provided by the electrodes of the stimulation zone.

5. The system of claim 4, the steps further comprises determining the weighted contribution of currents provided by the multiple electrodes by calculating a Euclidean distance from one of the multiple electrodes to at least one point of the stimulation zone.

6. The system of claim 4, the steps further comprises determining the weighted contribution of currents provided by the multiple electrodes, the current of each of the multiple electrodes is individually determined based on a generated field of neighbor electrodes.

7. The system of claim 4, the steps further comprises determining the weighted contribution of currents provided by the multiple electrodes, the current of each of the multiple electrodes is individually calculated by a numerical method.

8. The system of claim 7, wherein the weighted contribution of currents is determined by an algorithm to a benefit of power efficiency.

9. The method according to claim 8, further comprises the step of at least partially automatically determining a stimulation zone on the electrode array, or at least partially automatically selecting at least one electrode.

10. The method according to claim 9, wherein the weighted contribution of currents is determined by an algorithm to the benefit of power efficiency.

11. The system of claim 1, wherein the system further comprises at least one of a display, a controller, a programmer, a communication module, a telemetry module, a stimulation device, an electrode, a sensor and/or a sensor network.

12. The system of claim 1, the steps further comprising at least partially automatically determining a stimulation zone on the electrode array, or at least partially automatically selecting at least one electrode.

13. The system of claim 1, wherein the weighting of the electrode array is a current weighting.

14. A method for planning neuromodulation comprising the steps of:
   providing graphical information about an electrode array overlapped on an anatomical imaging of a patient, the graphical information comprises at least one target area; and determining, by receiving a selection of at least one of the at least one target area of the graphical information and translating the selection into a weighting of the electrode array based on the selection:

a stimulation zone on the electrode array;

non-targeted dorsal roots; and contribution of currents provided by the electrode array, such that a stimulation field created by the electrode array avoid activation of the non-targeted roots;

wherein the electrode array comprises multiple electrodes, or an implantation side for the electrode array comprises at least one target area;

wherein each of the multiple electrodes is capable of independently having a different waveform.

15. The method according to claim 14, wherein the graphical information about the electrode array comprises actual physical electrodes or virtual electrodes.

16. The method according to claim 15, further comprises a step of determining an equal contribution of currents provided by the electrodes of the stimulation zone.

17. The method according to claim 15, further comprises a step of determining a weighted contribution of currents provided by the electrodes of the stimulation zone.

18. The method according to claim 17, further comprises the step of determining the weighted contribution of currents provided by the multiple electrodes by calculating a Euclidean distance from one of the multiple electrodes to at least one point of the stimulation zone.

19. The method according to claim 17, further comprises the step of determining the weighted contributions of currents provided by the multiple electrodes, the current of each of the multiple electrodes is individually determined based on a generated field of neighbor electrodes.

20. The method according to claim 17, further comprises the step of determining the weighted contribution of currents provided by the multiple electrodes, the current of each of the multiple electrodes is individually calculated by a numerical method.

21. The method of claim 14, wherein the weighting of the electrode array is a current weighting.

\* \* \* \* \*